United States Patent
Kitamura

(10) Patent No.: US 8,378,336 B2
(45) Date of Patent: Feb. 19, 2013

(54) LIQUID CRYSTALLINE ORGANIC SEMICONDUCTOR MATERIAL AND ORGANIC ELECTRON DEVICE

(75) Inventor: Tetsu Kitamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 394 days.

(21) Appl. No.: 12/487,005

(22) Filed: Jun. 18, 2009

(65) Prior Publication Data

US 2009/0315025 A1 Dec. 24, 2009

(30) Foreign Application Priority Data

Jun. 19, 2008 (JP) ................................ 2008-160819

(51) Int. Cl.
*H01L 35/24* (2006.01)
(52) U.S. Cl. ................................. 257/40; 257/E51.001
(58) Field of Classification Search .................... 257/40, 257/E51.001
See application file for complete search history.

(56) References Cited

U.S. PATENT DOCUMENTS

| | | | | |
|---|---|---|---|---|
| 5,952,140 | A * | 9/1999 | Visser et al. | 430/58.5 |
| 2001/0002703 | A1 * | 6/2001 | Koyama | 257/40 |
| 2005/0104037 | A1 * | 5/2005 | Lazarev et al. | 252/299.01 |
| 2006/0054884 | A1 * | 3/2006 | Maeda et al. | 257/40 |

OTHER PUBLICATIONS

Lin et al, "Field and temperature dependencies of free carrier photogeneration efficiencies of molecular glasses," J. Chem. Phys., 105 (19), Nov. 15, 1996, pp. 8490-8494.*
Lin et al, "Free carrier photogeneration in electron-donor, electron-acceptor, and bifunctional molecular glasses," Part of the SPIE Conference on Organic Photorefractive Materials III, Jul. 1998, vol. 3471, pp. 235-241.*
Jana Zaumseil, et al., "Electron and Ambipolar Transport in Organic Field-Effect Transistors," Chemical Reviews, 2007, pp. 1296-1323, vol. 107, No. 4.
Abhijit Basu Maelik, et al., "3.1 Design, Synthesis, and Transistor Performance of Organic Semiconductors," Organic Field-Effect Transistors, 2007, CRC Press, pp. 159-228.
Serap Gunes, et al., "Conjugated Polymer-Based Organic Solar Cells," Chemical Reviews, 2007, pp. 1324-1338, vol. 107, No. 4.
Yoshihito Kunugi, et al., "An ambipolar organic field-effect transistor using oligothiophene incorporated with two [60]fullerenes," Journal of Materials Chemistry, 2004, pp. 2840-2841, vol. 14.
Jean-Francois Nierengarten, et al., "Synthesis of a $C_{60}$-oligophenylenevinylene hybrid and its incorporation in a photovoltaic device," Chemical Communications, 1999, pp. 617-618.
Sabine Laschat, et al., "Discotic Liquid Crystals: From Tailor-Made Synthesis to Plastic Electronics," Angewandte Chemie International Edition, 2007, pp. 4832-4887, vol. 46.
Jens Cremer, et al., "Star-shaped perylene-oligothiophene-triphenylamine hybrid systems for photovoltaic applications," Journal of Materials Chemistry, 2006, pp. 874-884, vol. 16.

* cited by examiner

*Primary Examiner* — Anthony Ho
(74) *Attorney, Agent, or Firm* — Sughrue Mion, PLLC

(57) ABSTRACT

A liquid crystalline organic semiconductor material, having a compound having at least one bonding form selected from the group consisting of (p-type organic semiconductor compound residue)-(n-type organic semiconductor compound residue)-(p-type organic semiconductor compound residue), and (n-type organic semiconductor compound residue)-(p-type organic semiconductor compound residue)-(n-type organic semiconductor compound residue).

30 Claims, 5 Drawing Sheets

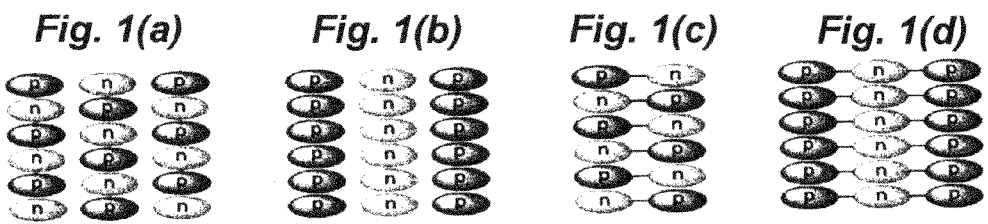
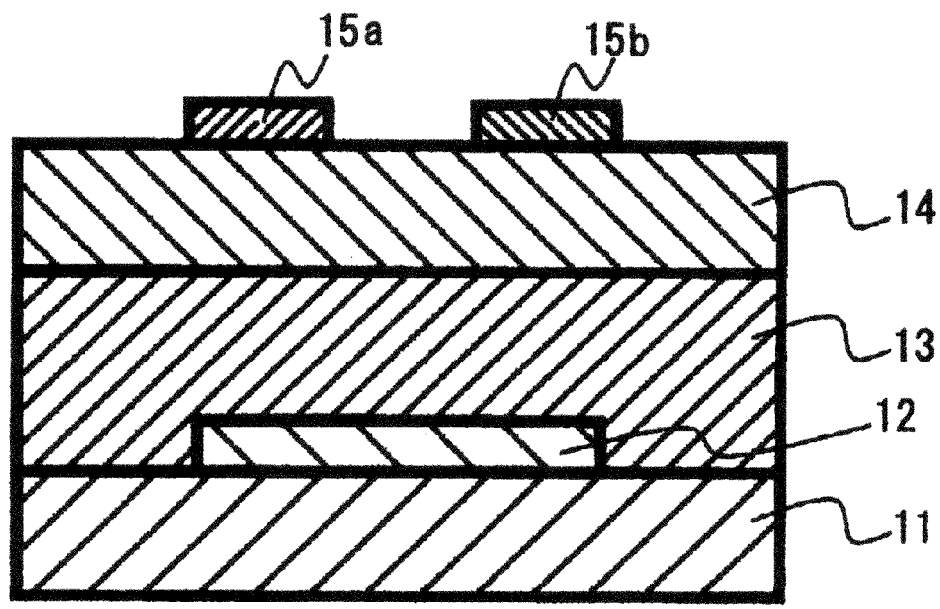

LIQUID CRYSTALLINE ORGANIC SEMICONDUCTOR MATERIAL AND ORGANIC ELECTRON DEVICE

FIELD OF THE INVENTION

The present invention relates to a novel liquid crystalline organic semiconductor material, a thin film containing the liquid crystalline organic semiconductor material, and an organic electronic device (in particular, an organic thin-film transistor or an organic thin-film photoelectric conversion device) using the liquid crystalline organic semiconductor material.

BACKGROUND OF THE INVENTION

With the arrival of a ubiquitous information society, information terminals need to be able to transfer information anytime, anywhere. For such a terminal, a flexible, light-weight, and inexpensive electronic device is required, but conventional electronic devices using an inorganic semiconductor material such as silicon do not sufficiently meet the requirement. Accordingly, in recent years, electronic devices using organic semiconductor materials have been intensively studied for satisfying such requirements (Chemical Reviews, 2007, 107, 1296 to 1323 and "Organic Field-Effect Transistors" (2007, CRC Press), pp. 159 to 228).

Organic semiconductor materials are classified into p-type organic semiconductors for transporting holes, and n-type organic semiconductors for transporting electrons in the same manner as inorganic semiconductor materials. When a p-type organic semiconductor material and an n-type organic semiconductor material are combined with each other, an ambipolar organic transistor (Chemical Reviews, 2007, 107, 1296 to 1323) and an organic photoelectric conversion device (Chemical Reviews, 2007, 107, 1324 to 1338) are obtained. Recently, it is reported that by use of a molecule wherein a p-type organic semiconductor compound residue and an n-type organic semiconductor compound residue are linked to each other through a covalent bond (hereinafter referred to as a "p-n linked molecule"), functions of the p-type organic semiconductor and n-type organic semiconductor can be performed with a single component by using the p-n linked molecule (Journal of Materials Chemistry, 2004, 14, 2840 to 2841 and Chemical Communications, 1999, 617 to 618).

The properties of an organic semiconductor material largely depend on the orientation/alignment state of the molecule thereof. In particular, in the case of using the p-n linked molecule, the above-mentioned function cannot be expressed unless a hole transporting path and an electron transporting path are both formed. Thus, it is important to control the orientation/alignment of the molecule. As the method for controlling the orientation/alignment of the molecule, the use of liquid crystallinity is effective (Angewandte Chemie International Edition, 2007, 46, 4832 to 4837). As an organic electronic device using the p-n linked molecule, an example of an organic thin-film photoelectric conversion device has been hitherto reported in which the following is used: a disc-form compound wherein a triphenylamine compound residue, which is a p-type organic semiconductor compound residue, and a peryleneimide compound residue, which is an n-type organic semiconductor compound residue, are linked together. However, the orientation/alignment order of the molecule is low. Therefore, a transporting path for two carrier species (holes and electrons) cannot be made of a single component by using the p-n linked molecule. Thus, it is reported that photoelectric conversion performance is expressed only in the case of using the p-n linked molecule as mixed with a fullerene compound which is an n-type organic semiconductor material (Journal of Materials Chemistry, 2006, 16, 874 to 884).

SUMMARY OF THE INVENTION

The present invention resides in A liquid crystalline organic semiconductor material, having a compound having at least one bonding form selected from the group consisting of (p-type organic semiconductor compound residue)-(n-type organic semiconductor compound residue)-(p-type organic semiconductor compound residue), and (n-type organic semiconductor compound residue)-(p-type organic semiconductor compound residue)-(n-type organic semiconductor compound residue).

Further, the present invention resides in a liquid crystal compound represented by any one of Formulae 1 to 3:

Formula 1

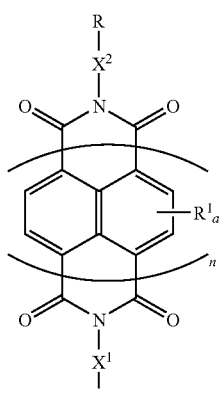

-continued

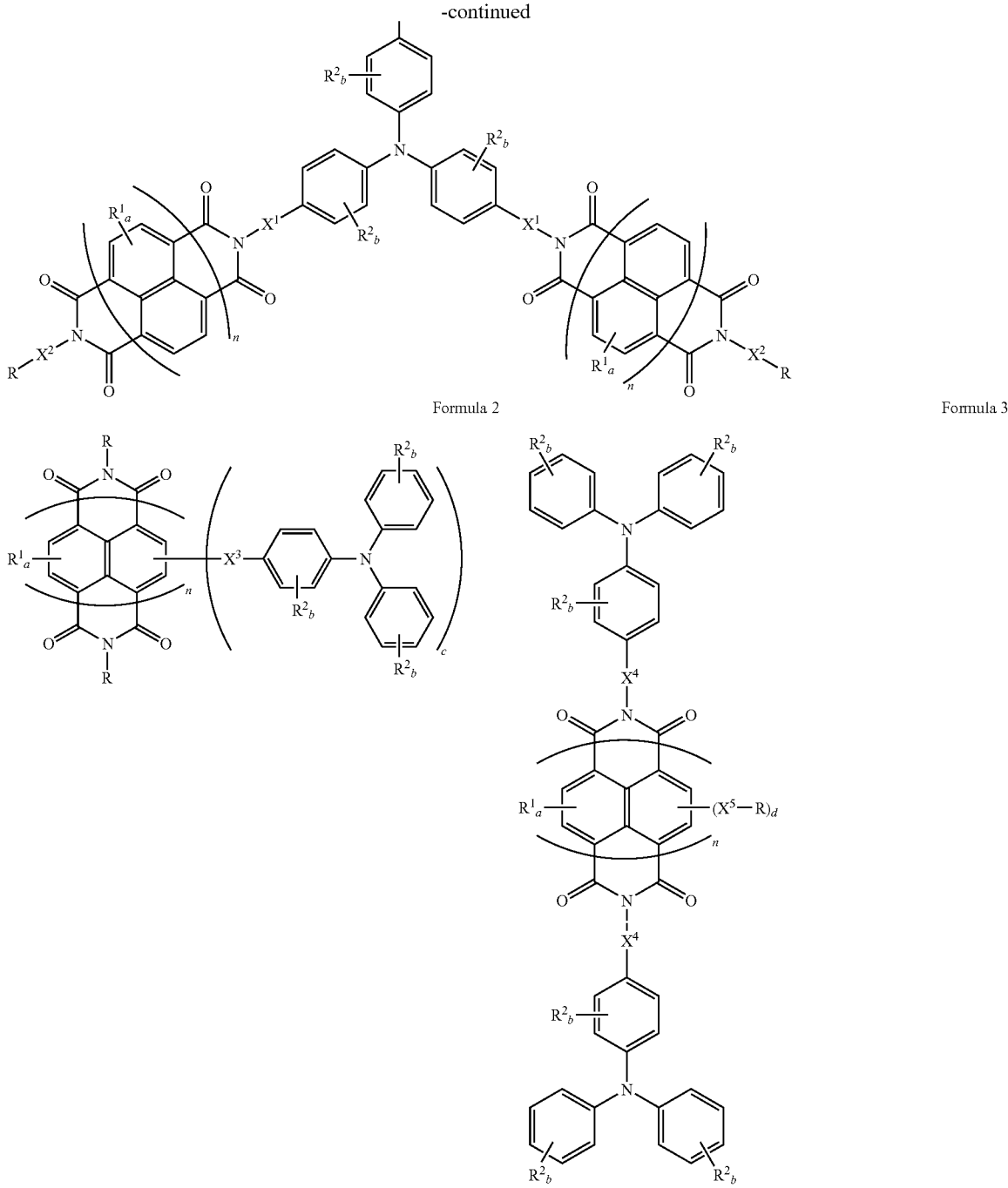

Formula 2

Formula 3 wherein R, $R^1$, and $R^2$ each independently represents a hydrogen atom or a substituent; $X_1$, $X_2$, $X_3$, $X_4$, and $X_5$ each independently represents a single bond or a divalent linking group; a, b, c, and d each denotes an integer; n denotes an integer of 1 to 3; in the case of a plurality of R, $R^1$, $R^2$, $X_1$, $X_2$, $X_3$, $X_4$, or $X_5$, they may be the same or different.

Further, the present invention resides in an organic semiconductor material for organic thin-film transistor, which has the liquid crystalline organic semiconductor material.

Further, the present invention resides in an organic semiconductor material for an organic thin-film photoelectric conversion device, which has the liquid crystalline organic semiconductor material.

Further, the present invention resides in a thin film having the liquid crystalline organic semiconductor material.

Further, the present invention resides in an organic electronic device, utilizing a liquid crystalline organic semiconductor material that has, in the molecule thereof, a p-type organic semiconductor compound residue and an n-type organic semiconductor compound residue.

Furthermore, the present invention resides in an organic electronic device, utilizing a liquid crystalline organic semiconductor material that has a compound having at least one bonding form of (p-type organic semiconductor compound residue)-(n-type organic semiconductor compound residue).

Other and further features and advantages of the invention will appear more fully from the following description, appropriately referring to the accompanying drawings.

BRIEF DESCRIPTION OF THE DRAWINGS

FIGS. 1(a) to 1(d) are explanatory views showing examples of the separately laminated structure of a p-n linked molecule.

FIG. 2 is a sectional view which schematically illustrates an example of the structure of the organic thin-film transistor device of the present invention.

In FIG. 5, 31 represents a substrate; 32 represents an electrode; 33 represents a insulator layer; 34a and 34b each represents a electrode; and 35 represents a semiconductor active layer.

FIGS. 6(a) and 6(b) show the characteristic in a p-type mode and that in an n-type mode, respectively.

DETAILED DESCRIPTION OF THE INVENTION

Figure 3:
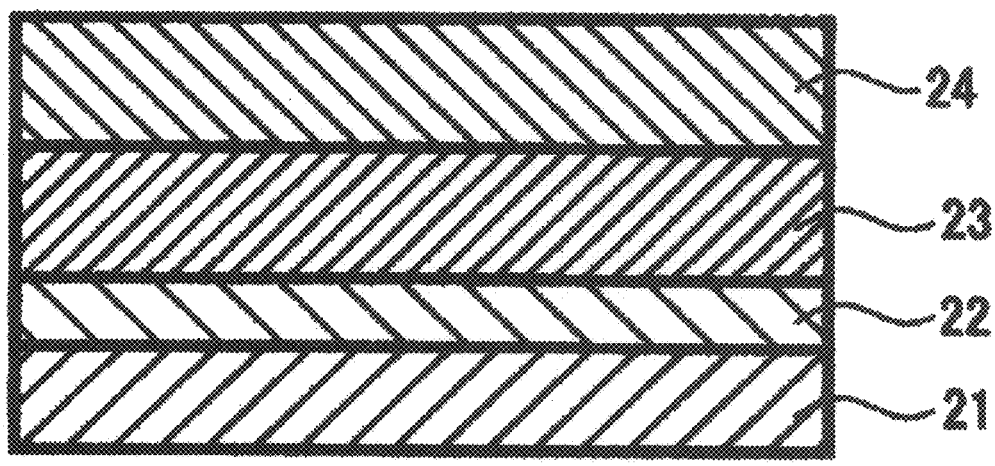
FIG. 3 is a sectional view which schematically illustrates an example of the structure of the organic thin-film photoelectric conversion device of the present invention.

The invention was made in light of the foregoing circumstances. The present invention is contemplated for providing a novel liquid crystalline organic semiconductor material which has a property of transporting two carrier species (holes and electrons) given by with a single component by using the p-n linked molecule and exhibits a photoelectric conversion property; and various kinds of organic electronic devices (in particular, an organic thin-film transistor and an organic thin-film photoelectric conversion device) using the liquid crystalline organic semiconductor material.

Through an assiduous study, the inventors discovered, as means for solving the problems, the following novel liquid-crystalline organic semiconductor material, thin film containing the liquid crystalline organic semiconductor material, and organic electronic device (in particular, an organic thin-film transistor or organic thin-film photoelectric conversion device) using the liquid crystalline organic semiconductor material.

According to the present invention, there are provided the following means:

(1) A liquid crystalline organic semiconductor material, having a compound having at least one bonding form selected from the group consisting of (p-type organic semiconductor compound residue)-(n-type organic semiconductor compound residue)-(p-type organic semiconductor compound residue), and (n-type organic semiconductor compound residue)-(p-type organic semiconductor compound residue)-(n-type organic semiconductor compound residue).

(2) The liquid crystalline organic semiconductor material described in the above item (1), wherein the length of a bivalent linking group for connecting the p-type organic semiconductor compound residue and the n-type organic semiconductor compound residue in the compound corresponds to 0 to 6 number of atom(s) provided that "0 number of atom(s)" means a single bond.

(3) The liquid crystalline organic semiconductor material described in the above item (1) or (2), wherein the phase transition temperature of the compound between a liquid crystal phase and an isotropic liquid phase in a temperature raising step is 200° C. or higher.

(4) The liquid crystalline organic semiconductor material described in any one of the above items (1) to (3), wherein the n-type organic semiconductor compound residue in the compound is any one of a naphthalenetetracarbonyl compound residue, perylenetetracarbonyl compound residue, and a terrylenetetracarbonyl compound residue.

(5) The liquid crystalline organic semiconductor material described in any one of the above items (1) to (4), wherein the p-type organic semiconductor compound residue in the compound is a triphenylamine residue.

(6) The liquid crystalline organic semiconductor material described in the above item (1), wherein the compound is represented by any one of Formulae 1 to 3:

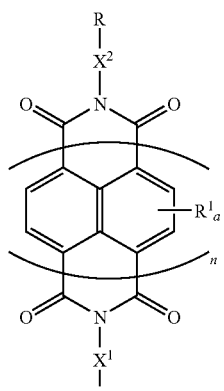

Formula 1

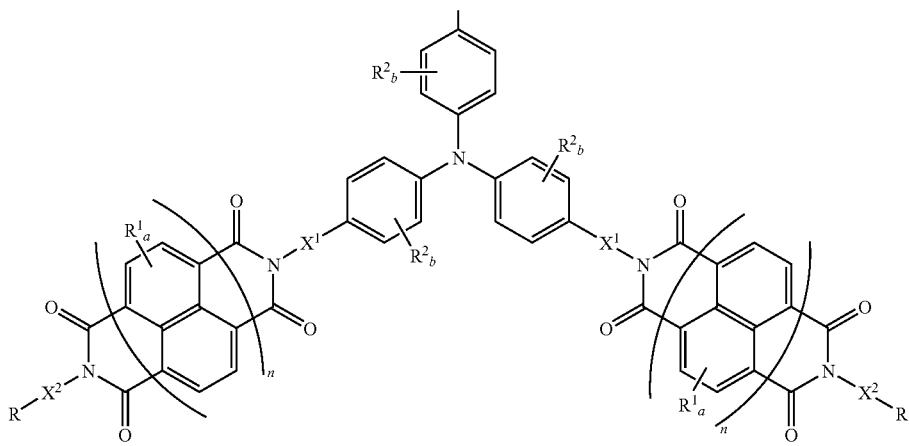

Formula 2

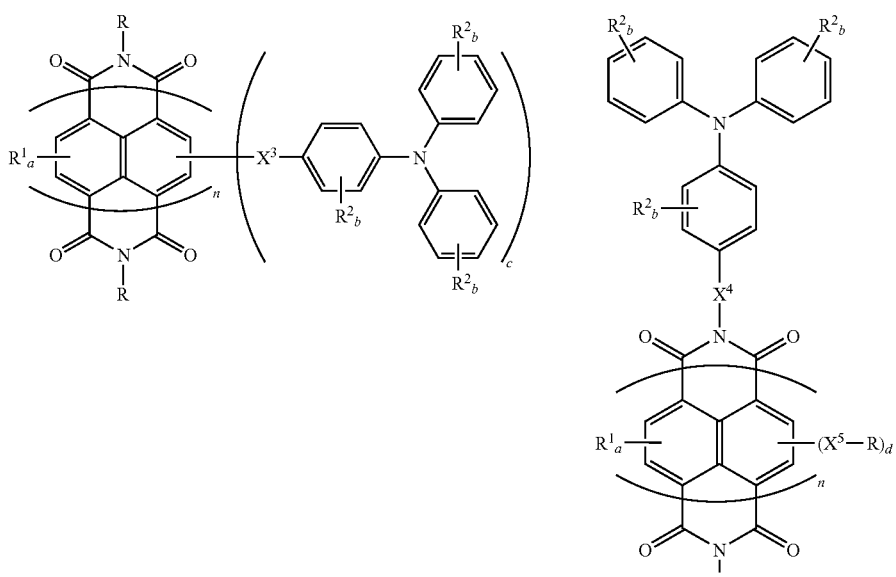

Formula 3

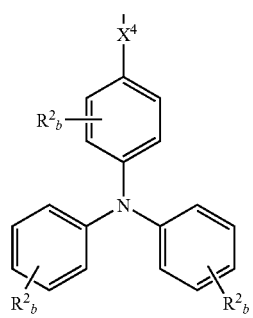

wherein R, $R^1$, and $R^2$ each independently represents a hydrogen atom or a substituent; $X_1$, $X_2$, $X_3$, $X_4$, and $X_5$ each independently represents a single bond or a divalent linking group; a, b, c, and d each denotes an integer; n denotes an integer of 1 to 3; in the case of a plurality of R, $R^1$, $R^2$, $X_1$, $X_2$, $X_3$, $X_4$, or $X_5$, they may be the same or different.

(7) The liquid crystalline organic semiconductor material described in the above item (6), wherein a length of the linking group represented by $X^1$, $X^3$ and $X^4$ each independently corresponds to 0 to 6 number of atom(s) provided that "number atom(s): 0" means a single bond.

(8) A liquid crystal compound represented by any one of Formulae 1 to 3:
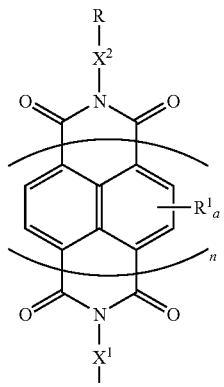
Formula 1
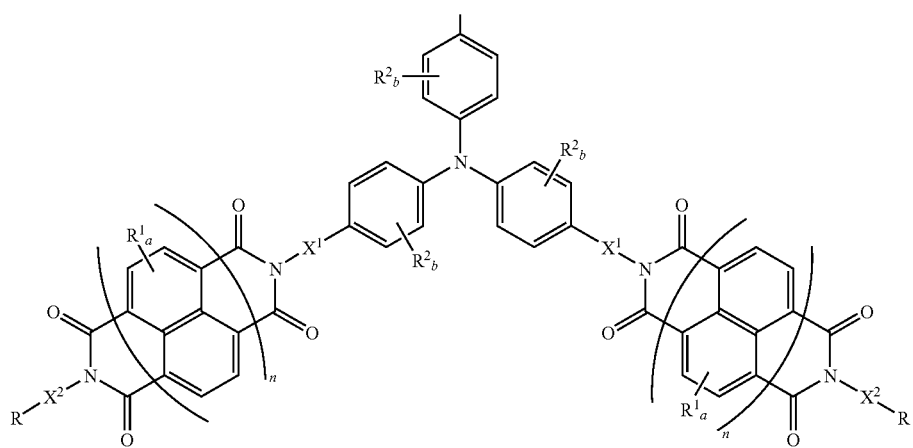
Formula 2
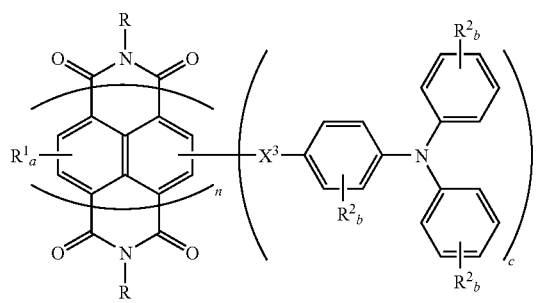
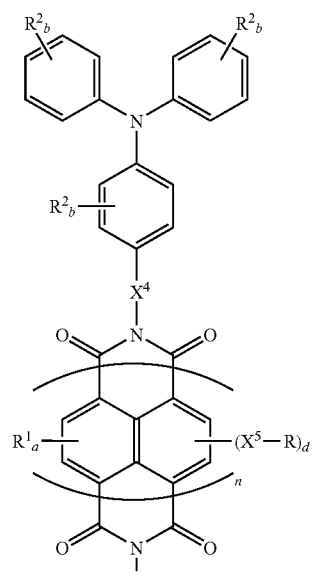
Formula 3

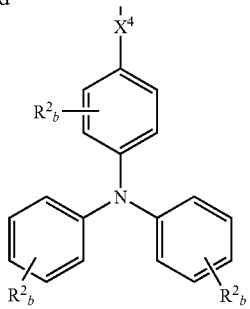

wherein R, R¹, and R² each independently represents a hydrogen atom or a substituent; $X_1$, $X_2$, $X_3$, $X_4$, and $X_5$ each independently represents a single bond or a divalent linking group; a, b, c, and d each denotes an integer; n denotes an integer of 1 to 3; in the case of a plurality of R, R¹, R², $X_1$, $X_2$, $X_3$, $X_4$, or $X_5$, they may be the same or different.

(9) An organic semiconductor material for organic thin-film transistor, which has the liquid crystalline organic semiconductor material described in any one of the above items (1) to (6).

(10) An organic semiconductor material for an organic thin-film photoelectric conversion device, which has the liquid crystalline organic semiconductor material described in any one of the above items (1) to (6).

(11) A thin film having the liquid crystalline organic semiconductor material described in any one of the above items (1) to (6).

(12) The thin film described in the above item (11), wherein the film is formed by a wet film forming process.

(13) The thin film described in the above item (11) or (12), wherein an average domain size of a liquid crystal or crystal of the liquid crystalline organic semiconductor material is larger than a thickness of the film.

(14) An organic electronic device, utilizing a liquid crystalline organic semiconductor material that has, in the molecule thereof, a p-type organic semiconductor compound residue and an n-type organic semiconductor compound residue.

(15) An organic electronic device, utilizing a liquid crystalline organic semiconductor material that has a compound having at least one bonding form of (p-type organic semiconductor compound residue)-(n-type organic semiconductor compound residue).

(16) The organic electronic device described in the above item (15), wherein the liquid crystalline organic semiconductor material has a compound having at least one bonding form selected from between (p-type organic semiconductor compound residue)-(n-type organic semiconductor compound residue)-(p-type organic semiconductor compound residue), and (n-type organic semiconductor compound residue)-(p-type organic semiconductor compound residue)-(n-type organic semiconductor compound residue).

(17) The organic electronic device described in any one of the above items (14) to (16), wherein an average domain size of a liquid crystal or crystal of the liquid crystalline organic semiconductor material is larger than a distance between the device's electrodes.

(18) The organic electronic device described in any one of the above items (14) to (17), wherein the organic electronic device is an organic thin-film transistor.

(19) The organic electronic device described in any one of the above items (14) to (17), wherein the organic electronic device is an organic thin-film photoelectric conversion device.

(20) The organic electronic device described in any one of the above items (14) to (19), wherein the organic electronic device has an electron-transporting buffer layer between at least one semiconductor active layer and at least one electrode.

(21) The organic electronic device described in any one of the above items (14) to (20), wherein the organic electronic device has a hole-transporting buffer layer between at least one semiconductor active layer and at least one electrode.

(22) The organic electronic device described in any one of the above items (14) to (21), wherein a film thickness of a semiconductor active layer is 1 nm or more and 1 μm or less.

(23) The organic electronic device described in any one of the above items (14) to (22), wherein a semiconductor active layer is formed by a wet film forming process.

(24) The organic electronic device described in any one of the above items (14) to (23), wherein the liquid crystalline organic semiconductor material is sealed in an inert gas atmosphere.

The liquid crystalline organic semiconductor material of the present invention (hereinafter also referred to as the organic semiconductor material of the present invention) has a bonding form that a p-type organic semiconductor compound residue and an n-type organic semiconductor compound residue are covalently linked to each other through a linking group.

In the present invention, the term "residue" is defined as a group obtained by removing, from a p-type organic semiconductor compound or n-type organic semiconductor compound, a necessary number of the hydrogen atom or substituent.

In the present invention, the term "p-type organic semiconductor compound residue" is defined as a group obtained by removing, from a p-type organic semiconductor compound exhibiting a hole mobility of $10^{-7}$ cm²/Vs or more in a solid state at room temperature, a necessary number of the hydrogen atom and substituent. The hole mobility can be measured by the field effect transistor (FET) method, the time of flight (TOF) method, the space charge limited current (SCLC) method, the time-resolved microwave absorption conductivity (TRMC) measurement method, or the like. The hole mobility is desirably higher. The hole mobility is preferably $10^{-7}$ cm²/Vs or more, more preferably $10^{-6}$ cm²/Vs or more, further more preferably $10^{-5}$ cm²/Vs or more. When a FET device is produced, it is particularly preferable to use a residue of a compound exhibiting a p-type property having the hole mobility of $10^{-5}$ cm²/Vs or more at room temperature.

The p-type organic semiconductor compound is not limited as far as satisfying the above-mentioned requirement. Examples of the p-type organic semiconductor compound include compounds described in "Organic Field-Effect Transistors" (published by CRC Press in 2007), pp. 159-228. From the viewpoint of a hole transporting capability and photoelectric conversion capability, the p-type organic semiconductor compound is preferably a condensed polycyclic compound (e.g., anthracene, tetracene, pentacene, anthradithiophene, and hexabenzocoronene), a triarylamine (e.g., triphenylamine), a 5-membered heterocyclic compound (e.g., oligothiophene and TTF analog), phthalocyanines, or porphyrins, more preferably a triarylamine or heterocyclic oligomer, and most preferably a triaylamine. Preferable specific examples of the p-type organic semiconductor compound are illustrated below. However, the p-type organic semiconductor compound is not limited thereto. (In formulae below, M represents a metal atom, or a hydrogen atom bonded to nitrogen atoms.)

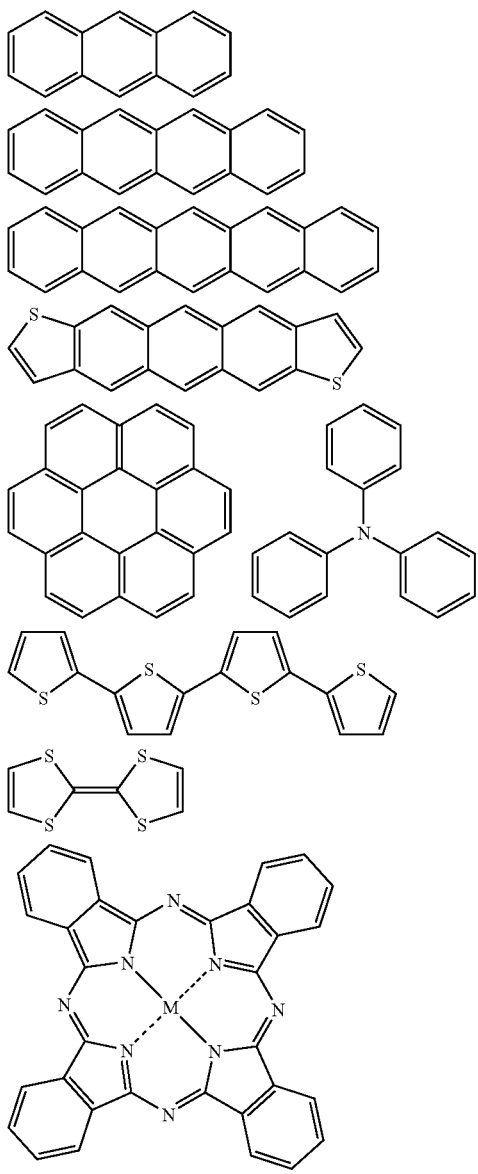

-continued

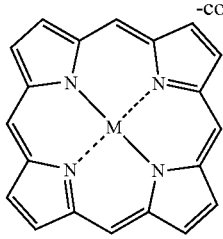

In the present invention, the term "n-type organic semiconductor compound residue" is defined as a group obtained by removing, from an n-type organic semiconductor compound exhibiting an electron mobility of $10^{-7}$ cm$^2$/Vs or more in a solid state at room temperature, a necessary number of the hydrogen atom and substituent. The electron mobility can be measured by the field effect transistor (FET) method, the time of flight (TOF) method, the space charge limited current (SCLC) method, the time-resolved microwave absorption conductivity (TRMC) measurement method, or the like. The electron mobility is desirably higher. The electron mobility is preferably $10^{-7}$ cm$^2$/Vs or more, more preferably $10^{-6}$ cm$^2$/Vs or more, further more preferably $10^{-5}$ cm$^2$/Vs or more. When a FET device is produced, it is particularly preferable to use a residue of a compound exhibiting an n-type property having the electron mobility of $10^{-5}$ cm$^2$/Vs or more at room temperature. The n-type organic semiconductor compound is not limited as far as satisfying the above-mentioned requirement. Examples of the n-type organic semiconductor compound include the compounds described in "Organic Field-Effect Transistors" (published by CRC Press in 2007), pp. 159 to 228. From the viewpoint of an electron transporting capability and a photoelectric conversion capability, the n-type organic semiconductor compound is preferably a naphthalenetetracarbonyl compound, a perylenetetracarbonyl compound, a terrylenetetracarbonyl compound, a fullerene compound, electron-deficient phthalocyanines (e.g., phthalocyanine to which 4 or more electron-withdrawing groups are bonded, and tetrapyridinoporphyrazine), or a TCNQ analogue (e.g., TCNQ, TCAQ, and dicyanomethylene-substituted terthienoquinoid compound), more preferably a naphthalenetetracarbonyl compound, a perylenetetracarbonyl compound, a terrylenetetracarbonyl compound, or a fullerene compound. From the viewpoint of easiness of the control of the orientation/alignment of the molecule, a naphthalenetetracarbonyl compound, a perylenetetracarbonyl compound, or a terrylenetetracarbonyl compound is particularly preferable. Preferable specific examples of the n-type organic semiconductor compound are illustrated below. However, the compound is not limited thereto. (In formulae below, R represents a substituent, and M represents a metal atom, or a hydrogen atom bonded to nitrogen atoms.)

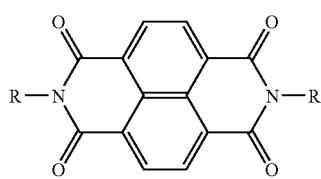

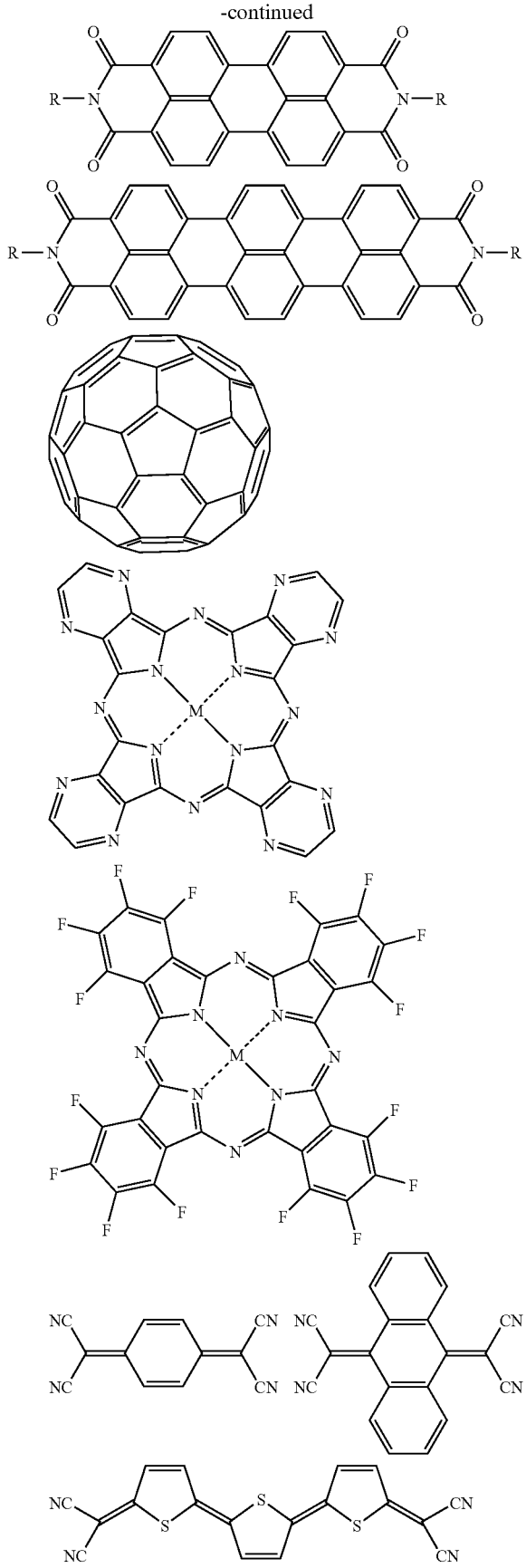

When a combination of a p-type organic semiconductor material with an n-type organic semiconductor material is used, it is usually very difficult to control the orientation/alignment and the relative positional relationship, of the two (the p-type organic semiconductor material and the n-type organic semiconductor material). By use of a bonding-form molecule wherein a p-type organic semiconductor compound residue and an n-type organic semiconductor compound residue are linked to each other through a covalent bond (hereinafter referred to as a "p-n linked molecule"), the relative positional relationship between the two can be controlled. By selecting a linking group for linking the two, the relative positional relationship (distance and angle) between the two can be decided, and the degree that a charge separation is readily caused and the degree that a charge recombination is readily caused can be controlled. As the linking group is shorter, an electron transfer between the p-type organic semiconductor compound residue and the n-type organic semiconductor compound residue is readily caused so that the charge separation is more readily caused. However, the charge recombination is also readily caused. When the ratio of the charge separation rate to the charge recombination rate is considered, the linking group is a group having a length corresponding preferably to 0 to 20 number of atom(s), more preferably 0 to 10, further more preferably 0 to 6 between the p-type and n-type organic semiconductor compound residues. It can be ascertained that a donation and reception of an electron are not caused between the p-n in a ground state by an absorption spectrum of a p-n linked molecule overlapping an absorption spectrum of the each residues. Moreover, intermolecular electron transfer can be ascertained by recognizing a matter that fluorescence from its fluorescent skeleton is extinguished. A charge separation state and the lifespan thereof can be observed by transient absorption spectrum measurement and electron spin resonance (ESR) measurement (J. Am. Chem. Soc., 2001, 123, 2607 to 2617). The charge separation lifespan is desirably longer. Known examples of the p-n linked molecule include the molecule described in J. Mater. Chem., 2006, 16, 874 to 884.

When a combination of a p-type organic semiconductor with an n-type organic semiconductor is used, the combination is generally apt to be in a lamination form of an alternately laminated type as illustrated in FIG. 1(a) for a stabilization by Madelung energy (Angew. Chem. Int. Ed., 2006, 45, 819 to 823). However, in order to establish a hole transporting path and an electron transporting path independently, it is necessary for the combination to be in a lamination form of a separately laminated type as illustrated in FIG. 1(b). In a conventional p-n linked molecule, it is considered that an alternately-laminated-type lamination form, wherein the molecules are reversely directed every other, is readily formed as illustrated in FIG. 1(c). It is thought that by bringing the symmetry of molecules into p-n-p or n-p-n, the molecules readily have a separately laminated structure as illustrated in FIG. 1(d). This structure is preferable. When a molecule has therein plural p-n-p bonds or n-p-n bonds and the shape of the molecule is a disc shape, or fan or sector shape, it is preferable that the molecule is a molecule having such a bonding form that p-type organic semiconductor compound residues and n-type organic semiconductor compound residues are concentrically arranged.

The organic semiconductor material of the present invention is a liquid crystalline material. In the present invention, the "liquid crystalline material" is defined as: a material exhibiting liquid crystallinity when a physical external stimulus (such as heating, cooling, the application of an electric field, a magnetic field, or a shearing force, or a combination thereof) is given to the material itself; or a material expressing a liquid crystallinity when the material is mixed with a solvent or a non-liquid-crystalline component. The liquid crystal phase is preferably a phase having a higher-level order. Thus, the liquid crystal phase is preferably a smectic phase, a discotic nematic phase, or a columnar phase, more preferably a discotic nematic phase or a columnar phase. The liquid crystal phase shown by a fan-shaped or disc-shaped molecule, as molecular shape, preferably has a higher order than that shown by a rodlike molecule. Examples of the method for checking a liquid crystallinity include observation with a polarizing microscope, differential scanning calorimetry (DSC), and X-ray diffraction measurement. Details thereof are described in "Handbook of Liquid Crystal (Ekisyo Binran))" (edited by Handbook of Liquid Crystal Editing Committee, and published by Maruzen Co., Ltd. in 2000), pp. 9 to 258. About liquid crystalline material, the orientation/alignment of a molecule thereof is more easily controlled, also at the time when the molecule is in a non-liquid-crystalline solid phase, than about an ordinary solid. Thus, as far as a liquid crystalline material is used in the present invention, the liquid crystal phase thereof is not necessarily used when the liquid crystalline material is actually used.

In order to make a molecule into a fan or disc shape, it is effective to introduce plural long-chain alkyl groups or oligoethyleneoxy groups thereinto. It is therefore preferable that the molecule to be used is linear or branched and has substituted or unsubstituted alkyl, alkoxy and/or oligoethyleneoxy groups, and the total number of carbon atoms in these groups is 24 or more (more preferably 36 or more). It is most preferable that the molecule is a linear or branched, has 6 to 30 carbon atoms, and has a benzene ring substituted with three out of substituted or unsubstituted alkyl, alkoxy and oligoethyleneoxy groups. About correlation between the shape of a molecule and the liquid crystallinity thereof, the above-mentioned "Liquid Crystal Handbook", pp. 259-447 can be referred to.

From the viewpoint of a thermal stability of the liquid crystal phase when using as an organic semiconductor material, the transition temperature of the organic semiconductor material between the liquid crystal phase and the isotropic liquid phase thereof is preferably higher when the temperature of the organic semiconductor material is raised. The transition temperature is preferably 100° C. or higher, more preferably 150° C. or higher, further more preferably 200° C. or higher.

The liquid crystalline organic semiconductor material of the present invention is particular preferably one represented by any one of Formulae 1 to 3.

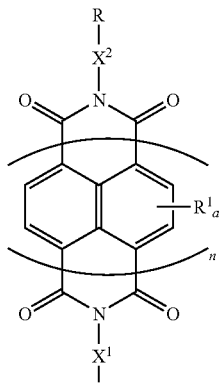

Formula 1

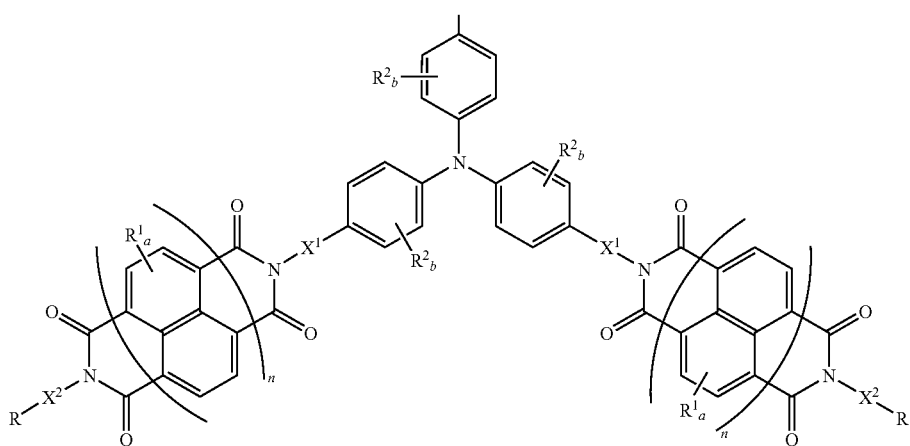

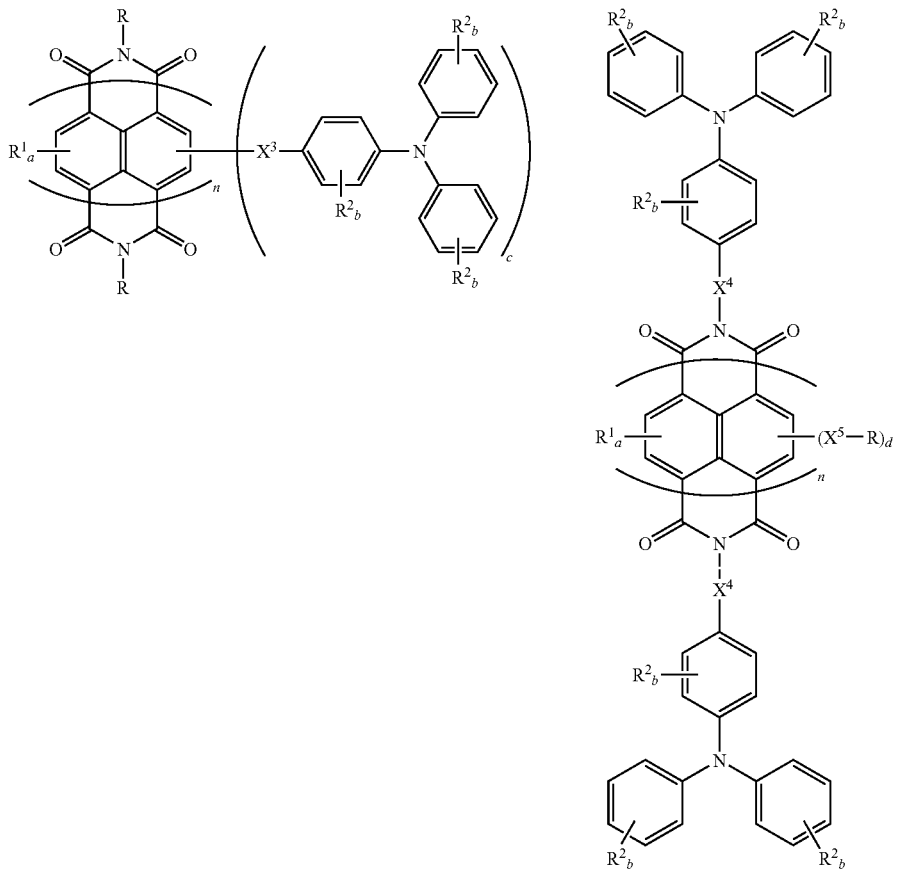

In Formulae 1 to 3, n is an integer of 1 to 3. The n-type organic semiconductor compound residue is a naphthalenebisimide residue (bisimide residue: a portion from a N atom of an imide to the opposite side N atom of the imide; the same matter is correspondingly applied to the following description) when n is 1; turns to a perylenebisimide residue when n is 2; or a terrylenebisimide residue when n is 3. The p-type organic semiconductor compound residue is a triphenylamine residue. In Formulae 1 to 3, a, b, c, and d each denotes an integer. a, b, c, and d each is the number of a hydrogen atom or a substituent which may be introduced onto the ring.

$R^1$ and $R^2$ each independently represent a hydrogen atom or a substituent. When $R^1$ and $R^2$ are appropriately selected, an orientation/alignment of a molecule a redox potential of a molecule, and the like can be controlled. The substituent $R^1$ or $R^2$ is not particularly limited, and can be selected from the substituents W described later. Among these substituents W, a hydrogen atom, a halogen atom, an alkyl group, an aryl group, a heterocyclic group, a cyano group, a hydroxyl group, a nitro group, an alkoxy group, an aryloxy group, a silyloxy group, a heterocyclic oxy group, an alkylthio group, an arylthio group, a heterocyclic thio group, an acyl group, an imido group, and a silyl group are preferable; a hydrogen atom, a halogen atom, an alkyl group, an aryl group, a heterocyclic group, a cyano group, a nitro group, an alkoxy group, an aryloxy group, a heterocyclic oxy group, an alkylthio group, an arylthio group, and a heterocyclic thio group are more preferable; a hydrogen atom, a halogen atom, an alkyl group, an aryl group, and a heterocyclic group are further preferable. a and b are integers representing the number of $R^1$ and $R^2$, respectively. The $R^1$s and $R^3$s may be the same or different from each other.

$X^1$, $X^2$, $X^3$, $X^4$ and $X^5$ each independently represent a single bond or a bivalent linking group. When $X^1$, $X^2$, $X^3$, $X^4$ and $X^5$ are appropriately selected, the followings can be controlled: the degree that electron transfer is readily caused between the p-type organic semiconductor compound residue and n-type organic semiconductor compound residue; the degree that a charge recombination is easily caused therebetween; a redox potential of a molecule; and a orientation/alignment of a molecule. $X^1$, $X^2$, $X^3$, $X^4$ and $X^5$ are each a group or bond wherein the smallest total number of atom(s) through which two bonding sites are linked to each other is preferably from 0 to 20, more preferably from 0 to 10, further more preferably from 0 to 6. When the number is zero, $X^1$, $X^2$, $X^3$, $X^4$ and $X^5$ each represent a single bond. Preferable examples of $X^1$, $X^2$, $X^3$, $X^4$ and $X^5$ include, but not to be limited to, a single bond, —$CH_2$— (1 number of atom(s)), —$CH_2CH_2$— (2 number of atom(s)), —$CH_2CH_2CH_2$— (3 number of atom(s)), —$CH_2CH_2CH_2CH_2$— (4 number of atom(s)), —$CH_2CH_2CH_2CH_2CH_2$— (5 number of atom(s)), —$CH_2CH_2CH_2CH_2CH_2CH_2$— (6 number of atom(s)), —O— (1 number of atom(s)), —$CH_2OCH_2$— (3 number of atom(s)), —$OCH_2CH_2O$— (4 number of atom(s)), —$OCH_2CH_2OCH_2CH_2$— (6 number of atom(s)), -Ph- (phenylene group, the bonding site may be o- (2 number of atom(s)), m- (3 number of atom(s)), or p- (4 number of atom(s)), —CO— (2 number of atom(s)), —COO— (2 number of atom(s)), —OCO— (2 number of atom(s)), —CONH— (2 number of atom(s)), —S— (1 number of atom(s)), —SO$_2$— (1 number of atom(s)), —NH— (1 number of atom(s)), —NHCO— (2 number of atom(s)), —C≡C— (2 number of atom(s)), —N=N— (2 number of atom(s)), —N=CH— (2 number of atom(s)), —CH=N— (2 number of atom(s)).

R represents a substituent necessary for bringing the molecular shape into a disc shape to express liquid crystallinity. R may be any substituent as far as liquid crystallinity is expressed. However, R is preferably a group having 12 or more carbon atoms. R is preferably an alkyl group, an alkoxy group, an oligoethyleneoxy group, or a benzene ring to which at least one of these groups is bonded. Rs in any one of the molecule of the material may be the same or different.

In the present invention, when specific sites of a substituent are called "groups", the site itself may not be substituted or may be substituted by one or more (to a possible maximum number) substituents. For example, "an alkyl group" means a substituted or unsubstituted alkyl group. Namely, the substituents which can be used in the compound for use in the present invention can be further substituted.

When the substituent represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, R15, and $R^{16}$ is set "W", the substituent represented by W may be any substituent and is not particularly limited, and, examples thereof include a halogen atom, an alkyl group (including a linear or branched alkyl group a cycloalkyl group, a bicycloalkyl group, and a tricycloalkyl group,), an alkenyl group (including a linear or branched alkenyl group a cycloalkenyl group and a bicycloalkenyl group), an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imido group, a phosphino group, a phosphinyl group, a phosphinyloxy group, a phosphinylamino group, a phosphono group, a silyl group, a hydrazino group, a ureido group, a boronic acid group(—B(OH)$_2$), a phosphate group(—OPO(OH)$_2$), a sulfate group(—OSO$_3$H), and other known substituents.

Specifically, the substituent represented by W represents the group as shown in the following items (1) to (48).

(1) Halogen atom (e.g., a fluorine atom, a chlorine atom, a bromine atom, an iodine atom)
(2) Alkyl group (which means a linear, branched or cyclic substituted or unsubstituted alkyl group, and examples of the alkyl group include the groups as shown in the following items (2-a) to (2-e))
(2-a) Alkyl group (alkyl group having preferably from 1 to 30 carbon atoms, more preferably from 5 to 20 carbon atoms, e.g., methyl, ethyl, n-propyl, isopropyl, tert-butyl, n-octyl, eicosyl, 2-chloroethyl, 2-cyanoethyl, 2-ethylhexyl)
(2-b) Cycloalkyl group (preferably a substituted or unsubstituted cycloalkyl group having from 3 to 30 carbon atoms, more preferably from 3 to 20 carbon atoms, e.g., cyclohexyl, cyclopentyl, 4-n-dodecyl-cyclohexyl)
(2-c) Bicycloalkyl group (preferably a substituted or unsubstituted bicycloalkyl group having from 5 to 30 carbon atoms, more preferably from 5 to 20 carbon atoms, e.g., bicyclo[1,2,2]heptan-2-yl, bicyclo[2,2,2]octan-3-yl)
(2-d) Tricycloalkyl group (preferably a substituted or unsubstituted tricycloalkyl group having from 7 to 30 carbon atoms, more preferably from 7 to 20 carbon atoms, e.g., 1-adamantyl)
(2-e) Alkyl group having a polycyclic structure The alkyl group in the substituents described below (for example, an alkyl group in an alkylthio group) means an alkyl group having such a concept and further includes an alkenyl group and an alkynyl group (3) Alkenyl group (which means a linear, branched or cyclic substituted or unsubstituted alkenyl group, and examples of the alkenyl group include the groups as shown in the following items (3-a) to (3-c))
(3-a) Alkenyl group (preferably a substituted or unsubstituted alkenyl group having from 2 to 30 carbon atoms, more preferably from 2 to 20 carbon atoms, e.g., vinyl, allyl, prenyl, geranyl, oreyl)
(3-b) Cycloalkenyl group (preferably a substituted or unsubstituted cycloalkenyl group having from 3 to 30 carbon atoms, more preferably from 3 to 20 carbon atoms, e.g., 2-cyclopenten-1-yl, 2-cyclohexen-1-yl)
(3-c) Bicycloalkenyl group (a substituted or unsubstituted bicycloalkenyl group, preferably a substituted or unsubstituted bicycloalkenyl group having from 5 to 30 carbon atoms, more preferably from 5 to 20 carbon atoms, e.g., bicyclo[2,2,1]hept-2-en-1-yl, bicyclo[2,2,2]oct-2-en-4-yl)
(4) Alkynyl group (preferably a substituted or unsubstituted alkynyl group having from 2 to 30 carbon atoms, more preferably from 2 to 20 carbon atoms, e.g., ethynyl, propargyl, trimethylsilylethynyl)
(5) Aryl group (preferably a substituted or unsubstituted aryl group having from 6 to 30 carbon atoms, more preferably from 6 to 20 carbon atoms, e.g., phenyl, p-tolyl, naphthyl, m-chlorophenyl, o-hexadecanoylaminophenyl, ferrocenyl)
(6) Heterocyclic group (preferably a monovalent group resultant from removing one hydrogen atom of a 5- or 6-membered substituted or unsubstituted aromatic or non-aromatic heterocyclic compound, more preferably a 5- or 6-membered aromatic heterocyclic group having from 2 to 50 carbon atoms, the heteroatom includes N, O, S, Se, Te, P, Si, and Ge. (e.g., 2-furyl, 2-thienyl, 2-pyrimidinyl, 2-benzothiazolyl; the heterocyclic group may also be a cationic heterocyclic group such as 1-methyl-2-pyridinio and 1-methyl-2-quinolinio))
(7) Cyano group
(8) Hydroxyl group
(9) Nitro group
(10) Carboxyl group
(11) Alkoxy group (preferably a substituted or unsubstituted alkoxy group having from 1 to 30 carbon atoms, more preferably from 1 to 20 carbon atoms, e.g., methoxy, ethoxy, isopropoxy, tert-butoxy, n-octyloxy, 2-methoxyethoxy)

(12) Aryloxy group (preferably a substituted or unsubstituted aryloxy group having from 6 to 30 carbon atoms, more preferably from 6 to 20 carbon atoms, e.g., phenoxy, 2-methylphenoxy, 4-tert-butylphenoxy, 3-nitrophenoxy, 2-tradecanoylaminophenoxy)

(13) Silyloxy group (preferably a silyloxy group having from 3 to 30 carbon atoms, more preferably from 3 to 20 carbon atoms, e.g., trimethylsilyloxy, tert-butyldimethylsilyloxy)

(14) Heterocyclic oxy group (preferably a substituted or unsubstituted heterocyclic oxy group having from 2 to 30 carbon atoms, more preferably from 2 to 20 carbon atoms, e.g., 1-phenyltetrazol-5-oxy, 2-tetrahydropyranyloxy)

(15) Acyloxy group (preferably a formyloxy group, a substituted or unsubstituted alkylcarbonyloxy group having from 2 to 30 carbon atoms, more preferably from 2 to 20 carbon atoms, or a substituted or unsubstituted arylcarbonyloxy group having from 6 to 30 carbon atoms, more preferably from 6 to 20 carbon atoms, e.g., formyloxy, acetyloxy, pivaloyloxy, stearoyloxy, benzoyloxy, p-methoxyphenylcarbonyloxy)

(16) Carbamoyloxy group (preferably a substituted or unsubstituted carbamoyloxy group having from 1 to 30 carbon atoms, more preferably from 1 to 20 carbon atoms, e.g., N,N-dimethylcarbamoyloxy, N,N-diethylcarbamoyloxy, morpholinocarbonyloxy, N,N-di-n-octylaminocarbonyloxy, N-n-octylcarbamoyloxy)

(17) Alkoxycarbonyloxy group (preferably a substituted or unsubstituted alkoxycarbonyloxy group having from 2 to 30 carbon atoms, more preferably from 2 to 20 carbon atoms, e.g., methoxycarbonyloxy, ethoxycarbonyloxy, tert-butoxycarbonyloxy, n-octylcarbonyloxy)

(18) Aryloxycarbonyloxy group (preferably a substituted or unsubstituted aryloxycarbonyloxy group having from 7 to 30 carbon atoms, more preferably from 7 to 20 carbon atoms, e.g., phenoxycarbonyloxy, p-methoxyphenoxycarbonyloxy, p-n-hexadecyloxyphenoxycarbonyloxy)

(19) Amino group (preferably an amino group, a substituted or unsubstituted alkylamino group having from 1 to 30 carbon atoms, more preferably from 7 to 20 carbon atoms, or a substituted or unsubstituted anilino group having from 6 to 30 carbon atoms, e.g., amino, methylamino, dimethylamino, anilino, N-methyl-anilino, diphenylamino)

(20) Ammonio group (preferably an ammonio group or an ammonio group substituted by a substituted or unsubstituted alkyl, aryl or heterocyclic group having from 1 to 30 carbon atoms, more preferably from 1 to 20 carbon atoms, e.g., trimethylammonio, triethylammonio, diphenylmethylammonio)

(21) Acylamino group (preferably a formylamino group, a substituted or unsubstituted alkylcarbonylamino group having from 1 to 30 carbon atoms, more preferably from 1 to 20 carbon atoms, or a substituted or unsubstituted arylcarbonylamino group having from 6 to 30 carbon atoms, e.g., formylamino, acetylamino, pivaloylamino, lauroylamino, benzoylamino, 3,4,5-tri-n-octyloxyphenylcarbonylamino)

(22) Aminocarbonylamino group (preferably a substituted or unsubstituted aminocarbonylamino group having from 1 to 30 carbon atoms, more preferably from 1 to 20 carbon atoms, e.g., carbamoylamino, N,N-dimethylaminocarbonylamino, N,N-diethylaminocarbonylamino, morpholinocarbonylamino)

(23) Alkoxycarbonylamino group (preferably a substituted or unsubstituted alkoxycarbonylamino group having from 2 to 30 carbon atoms, more preferably from 2 to 20 carbon atoms, e.g., methoxycarbonylamino, ethoxycarbonylamino, tert-butoxycarbonylamino, n-octadecyloxycarbonylamino, N-methyl-methoxycarbonylamino)

(24) Aryloxycarbonylamino group (preferably a substituted or unsubstituted aryloxycarbonylamino group having from 7 to 30 carbon atoms, more preferably from 7 to 20 carbon atoms, e.g., phenoxycarbonylamino, p-chlorophenoxycarbonylamino, m-(n-octyloxy) phenoxycarbonylamino)

(25) Sulfamoylamino group (preferably a substituted or unsubstituted sulfamoylamino group having from 0 to 30 carbon atoms, more preferably from 0 to 20 carbon atoms, e.g., sulfamoylamino, N,N-dimethylaminosulfonylamino, N-n-octylamninosulfonylamino)

(26) Alkyl- or aryl-sulfonylamino group (preferably a substituted or unsubstituted alkylsulfonylamino group having from 1 to 30 carbon atoms, more preferably from 1 to 20 carbon atoms, or a substituted or unsubstituted arylsulfonylamino group having from 6 to 30 carbon atoms, e.g., methylsulfonylamino, butylsulfonylamino, phenylsulfonylamino, 2,3,5-trichlorophenylsulfonylamino, p-methylphenylsulfonylamino)

(27) Mercapto group

(28) Alkylthio group (preferably a substituted or unsubstituted alkylthio group having from 1 to 30 carbon atoms, more preferably from 1 to 20 carbon atoms, e.g., methylthio, ethylthio, n-hexadecylthio)

(29) Arylthio group (preferably a substituted or unsubstituted arylthio group having from 6 to 30 carbon atoms, more preferably from 6 to 20 carbon atoms, e.g., phenylthio, p-chlorophenylthio, m-methoxyphenylthio)

(30) Heterocyclic thio group (preferably a substituted or unsubstituted heterocyclic thio group having from 2 to 30 carbon atoms, more preferably from 2 to 20 carbon atoms, e.g., 2-benzothiazolylthio, 1-phenyltetrazol-5-ylthio)

(31) Sulfamoyl group (preferably a substituted or unsubstituted sulfamoyl group having from 0 to 30 carbon atoms, more preferably from 0 to 20 carbon atoms, e.g., N-ethylsulfamoyl, N-(3-dodecyloxypropyl)sulfamoyl, N,N-dimethylsulfamoyl, N-acetylsulfamoyl, N-benzoylsulfamoyl, N-(N'-phenylcarbamoyl)sulfamoyl)

(32) Sulfo group

(33) Alkyl- or aryl-sulfinyl group (preferably a substituted or unsubstituted allylsulfinyl group having from 1 to 30 carbon atoms, more preferably from 1 to 20 carbon atoms, or preferably a substituted or unsubstituted arylsulfmyl group having from 6 to 30 carbon atoms, more preferably from 6 to 20 carbon atoms e.g., methylsulfinyl, ethylsulfmyl, phenylsulfinyl, p-methylphenylsulfinyl)

(34) Alkyl- or aryl-sulfonyl group (preferably a substituted or unsubstituted alkylsulfonyl group having from 1 to 30 carbon atoms, more preferably from 1 to 20 carbon atoms, or preferably a substituted or unsubstituted arylsulfonyl group having from 6 to 30 carbon atoms, more preferably from 6 to 20 carbon atoms e.g., methylsulfonyl, ethylsulfonyl, phenylsulfonyl, p-methylphenylsulfonyl)

(35) Acyl group (preferably a formyl group, a substituted or unsubstituted alkylcarbonyl group having from 2 to 30 carbon atoms, more preferably from 2 to 20 carbon atoms, a substituted or unsubstituted arylcarbonyl group having from 7 to 30 carbon atoms, more preferably from 7 to 20 carbon atoms, or a substituted or unsubstituted heterocyclic carbonyl group having from 4 to 30 carbon atoms, more preferably from 4 to 20 carbon atoms and being bonded to a carbonyl group through a carbon atom, e.g., acetyl, pivaloyl, 2-chloroacetyl, stearoyl, benzoyl, p-n-octyloxyphenylcarbonyl, 2-pyridylcarbonyl, 2-fulylcarbonyl)

(36) Aryloxycarbonyl group (preferably a substituted or unsubstituted aryloxycarbonyl group having from 7 to 30 carbon atoms, more preferably from 7 to 20 carbon atoms, e.g., phenoxycarbonyl, o-chlorophenoxycarbonyl, m-nitrophenoxycarbonyl, p-tert-butylphenoxycarbonyl)

(37) Alkoxycarbonyl group (preferably a substituted or unsubstituted alkoxycarbonyl group having from 2 to 30 carbon atoms, more preferably from 2 to 20 carbon atoms, e.g., methoxycarbonyl, ethoxycarbonyl, tert-butoxycarbonyl, n-octadecyloxycarbonyl)

(38) Carbamoyl group (preferably a substituted or unsubstituted carbamoyl group having from 1 to 30 carbon atoms, more preferably from 1 to 20 carbon atoms, e.g., carbamoyl, N-methylcarbamoyl, N,N-dimethylcarbamoyl, N,N-di-n-octylcarbamoyl, N-(methylsulfonyl)-carbamoyl)

(39) Aryl- or heterocyclic-azo group (preferably a substituted or unsubstituted arylazo group having from 6 to 30 carbon atoms, more preferably from 6 to 20 carbon atoms, or a substituted or unsubstituted heterocyclic-azo group having from 2 to 30 carbon atoms, e.g., phenylazo, p-chlorophenylazo, 5-ethylthio-1,3,4-thiadiazol-2-ylazo)

(40) Imido group (preferably N-succinimido, N-phthalimido)

(41) Phosphino group (preferably a substituted or unsubstituted phosphino group having from 2 to 30 carbon atoms, more preferably from 2 to 20 carbon atoms, e.g., dimethylphosphino, diphenylphosphino, methylphenoxyphosphino)

(42) Phosphinyl group (preferably a substituted or unsubstituted phosphinyl group having from 2 to 30 carbon atoms, more preferably from 2 to 20 carbon atoms, e.g., phosphinyl, dioctyloxyphosphinyl, diethoxyphosphinyl)

(43) Phosphinyloxy group (preferably a substituted or unsubstituted phosphinyloxy group having from 2 to 30 carbon atoms, more preferably from 2 to 20 carbon atoms, e.g., diphenoxyphosphinyloxy, dioctyloxyphosphinyloxy)

(44) Phosphinylamino group (preferably a substituted or unsubstituted phosphinylamino group having from 2 to 30 carbon atoms, more preferably from 2 to 20 carbon atoms, e.g., dimethoxyphosphinylamino, dimethylaminophosphinylamino)

(45) Phospho group

(46) Silyl group (preferably a substituted or unsubstituted silyl group having from 3 to 30 carbon atoms, more preferably from 3 to 20 carbon atoms, e.g., trimethylsilyl, triethylsilyl, tri(iso-propyl)silyl, tert-butyldimethylsilyl, phenyldimethylsilyl)

(47) Hydrazino group (preferably a substituted or unsubstituted hydrazino group having from 0 to 30 carbon atoms, more preferably from 0 to 20 carbon atoms, e.g., trimethylhydrazino)

(48) Ureido group (preferably a substituted or unsubstituted ureido group having from 0 to 30 carbon atoms, more preferably from 0 to 20 carbon atoms, e.g., N,N-dimethylureido)

Two substituents represented by W may also condense to form a ring, e.g., an aromatic or non-aromatic hydrocarbon ring, a heterocyclic ring or a polycyclic condensed ring formed by the combination of these rings, e.g., a benzene ring, a naphthalene ring, an anthracene ring, a phenanthrene ring, fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, a indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring, a phenazine ring. Among these, a benzene ring, a pyrrole ring, a furan ring, a thiophene ring, an imidazole ring, an oxazole ring, a thiazole ring, a pyridine ring, and a pyrazine ring are preferable.

Among these substituents W, those having a hydrogen atom may be deprived of the hydrogen atom and substituted by the above-described substituent. Examples of these substituents include —$CONHSO_2$— group (sulfonylcarbamoyl group, carbonylsulfamoyl group), —CONHCO— group (carbonylcarbamoyl group), and —$SO_2NHSO_2$13 group (sulfonylsulfamoyl group). Specific examples thereof include an alkylcarbonylaminosulfonyl group (e.g., acetylaminosulfonyl group), an arylcarbonylaminosulfonyl group (e.g., benzoylaminosulfonyl group), an alkylsulfonylaminocarbonyl group (e.g., methylsulfonylaminocarbonyl group), and an arylsulfonylaminocarbonyl group (e.g., p-methylphenylsulfonylaminocarbonyl group).

Preferable specific examples of the liquid crystalline organic semiconductor material of the present invention are shown in the followings, but the present invention is not limited thereto.

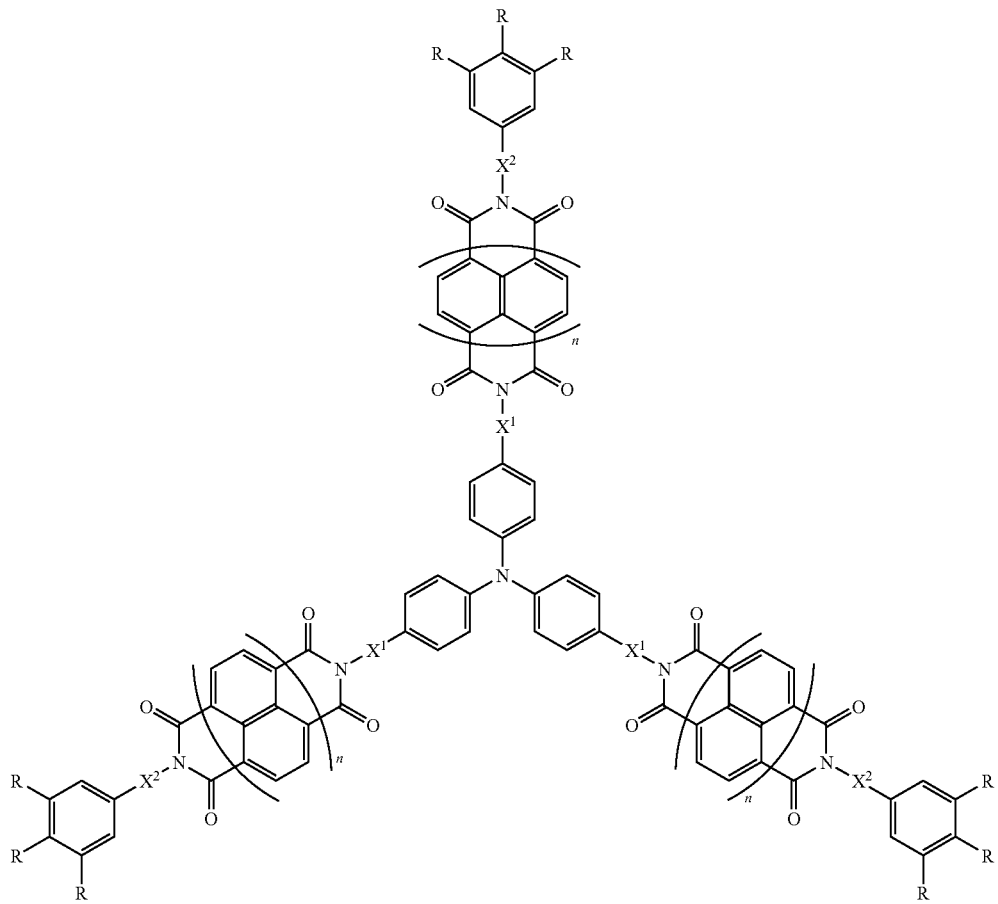

| Compound | $X^1$ | $X^2$ | n | R |
| --- | --- | --- | --- | --- |
| Exemplified compound 1 | — | — | 1 | $O(CH_2)_7CH_3$ |
| Exemplified compound 2 | — | — | 1 | $O(CH_2)_{11}CH_3$ |
| Exemplified compound 3 | — | — | 1 | $O(CH_2)_{17}CH_3$ |
| Exemplified compound 4 | — | — | 1 | $(CH_2)_{11}CH_3$ |
| Exemplified compound 5 | — | — | 1 | $(CF_2)_{11}CF_3$ |
| Exemplified compound 6 | — | — | 1 | $O(CH_2CH_2O)_4CH_3$ |
| Exemplified compound 7 | — | — | 1 | $O(CH_2)_{11}OCOCH=CH_2$ |
| Exemplified compound 8 | $CH_2$ | — | 1 | $O(CH_2)_{11}CH_3$ |
| Exemplified compound 9 | — | $CH_2$ | 1 | $O(CH_2)_{11}CH_3$ |
| Exemplified compound 10 | $CH_2$ | $CH_2$ | 1 | $O(CH_2)_{11}CH_3$ |
| Exemplified compound 11 | $CH_2CH_2$ | $CH_2CH_2$ | 1 | $O(CH_2)_{11}CH_3$ |
| Exemplified compound 12 | 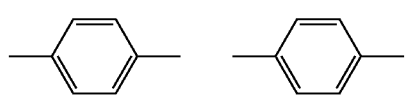 | | 1 | $O(CH_2)_{11}CH_3$ |
| Exemplified compound 13 | — | — | 2 | $O(CH_2)_{11}CH_3$ |

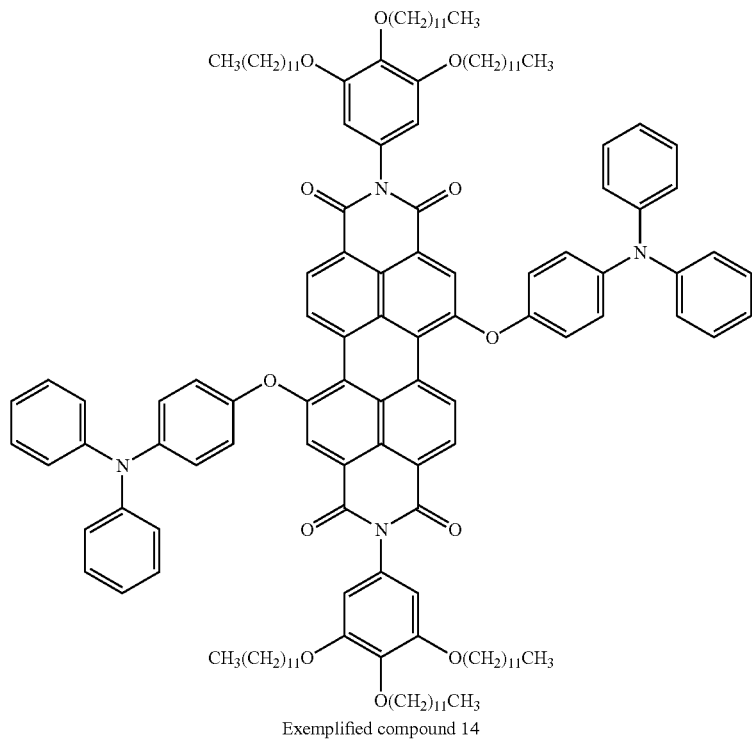
Exemplified compound 14
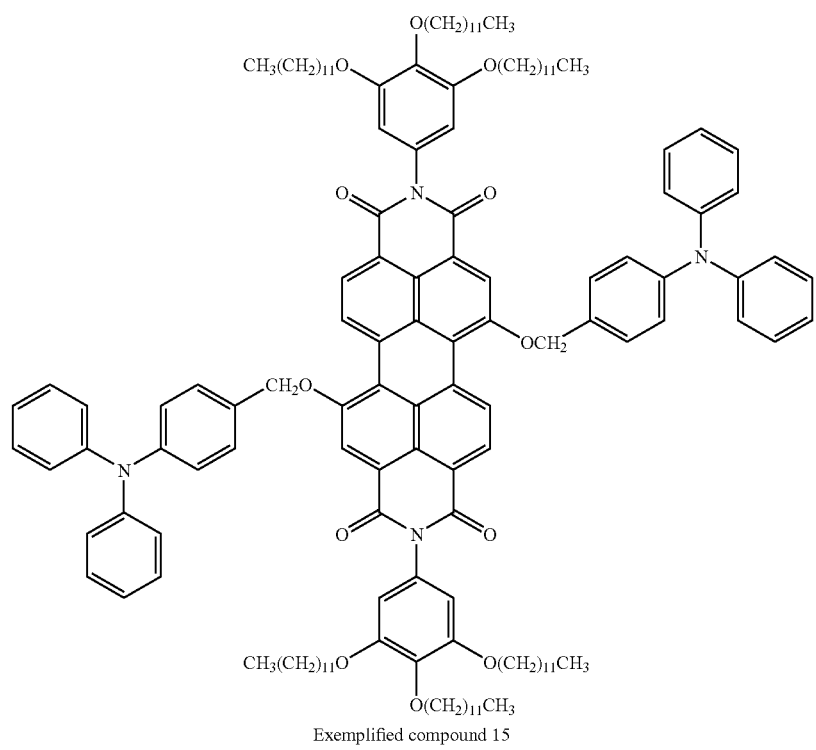
Exemplified compound 15

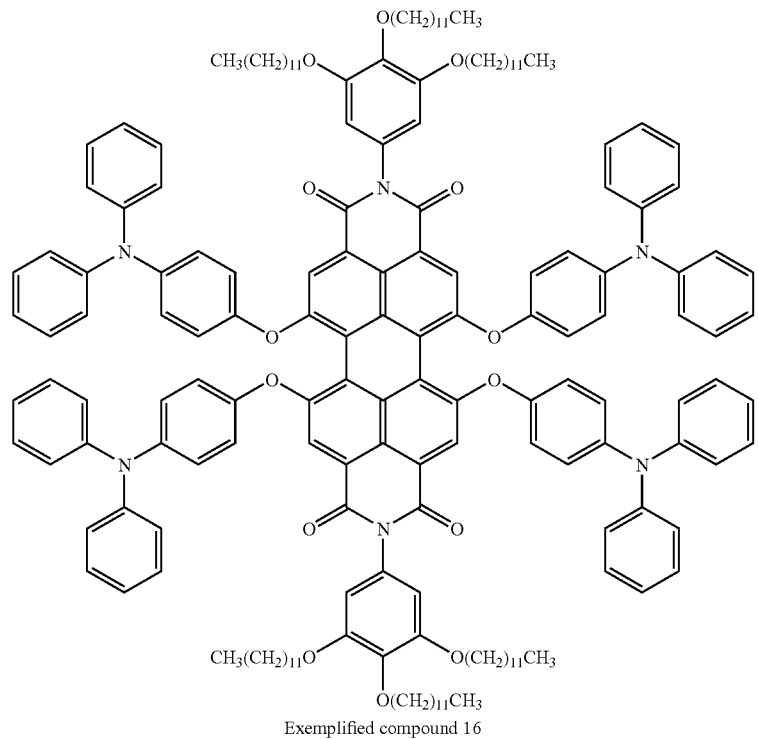
Exemplified compound 16
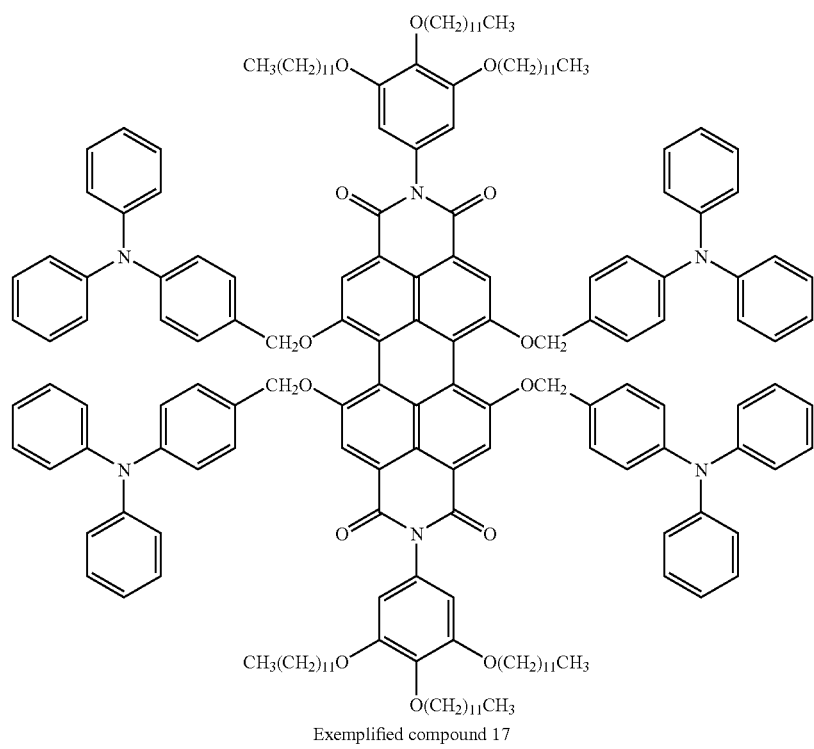
Exemplified compound 17

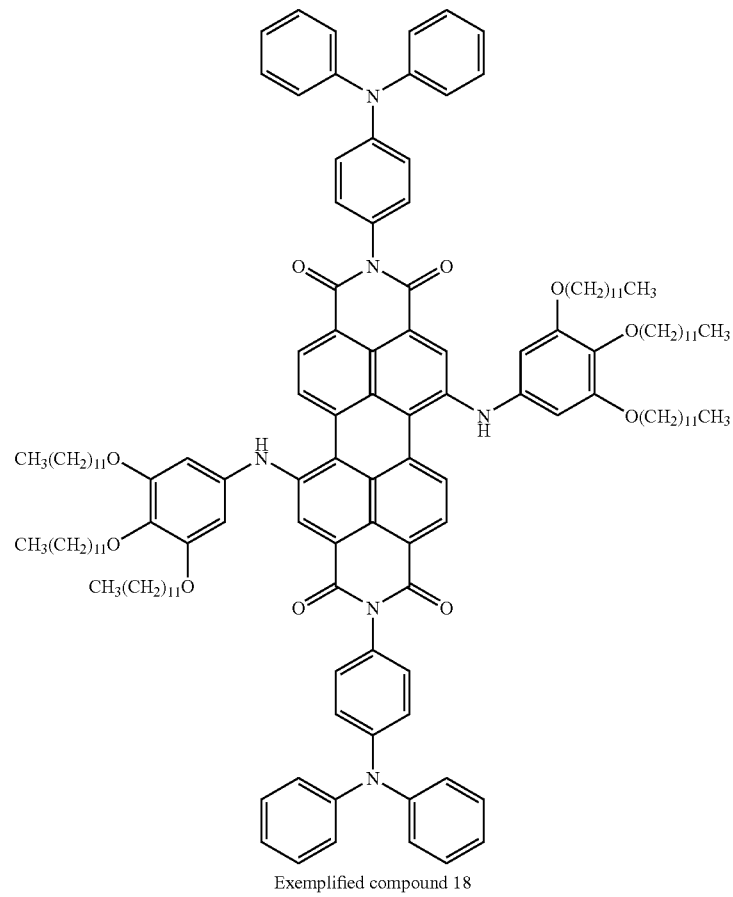
Exemplified compound 18

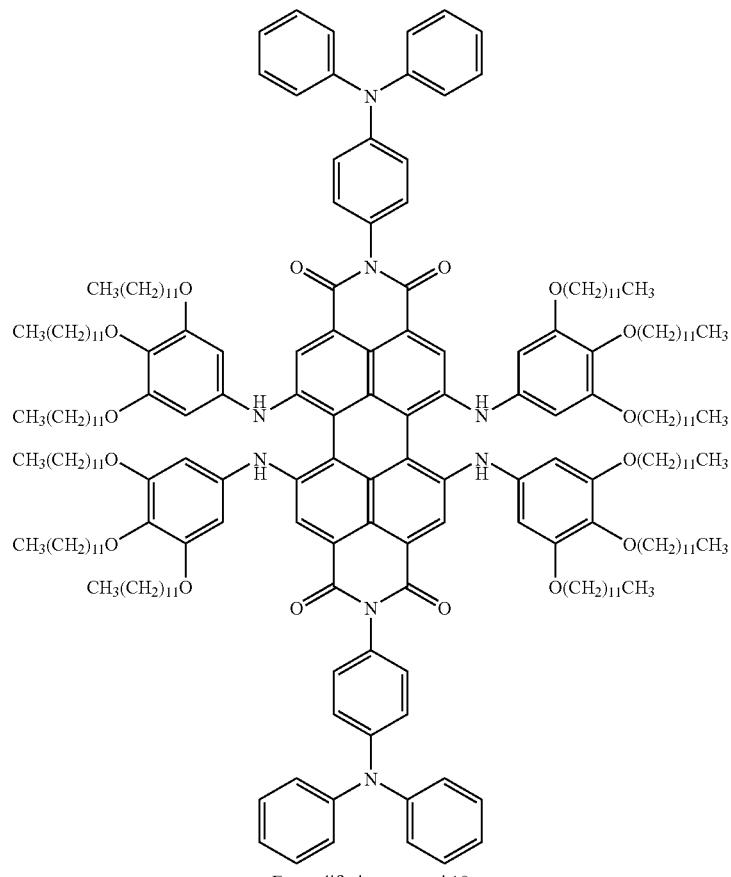
Exemplified compound 19
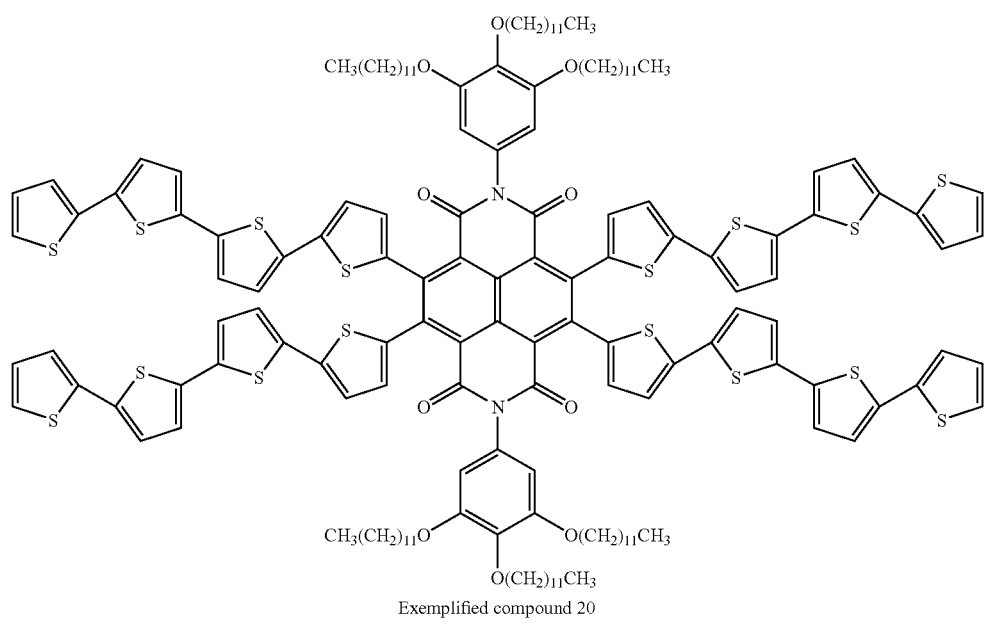
Exemplified compound 20

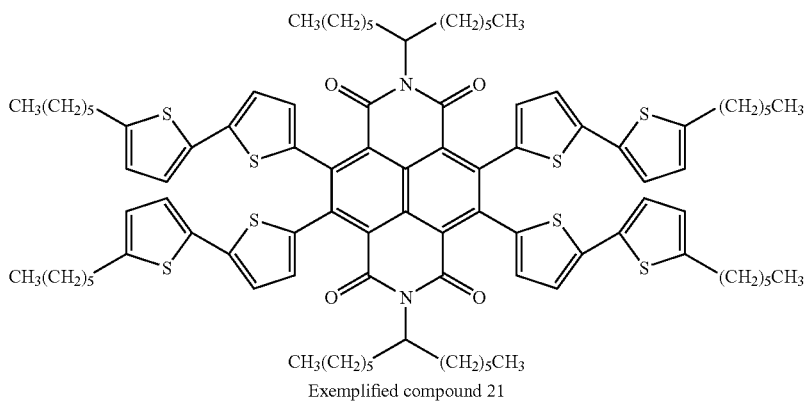
Exemplified compound 21

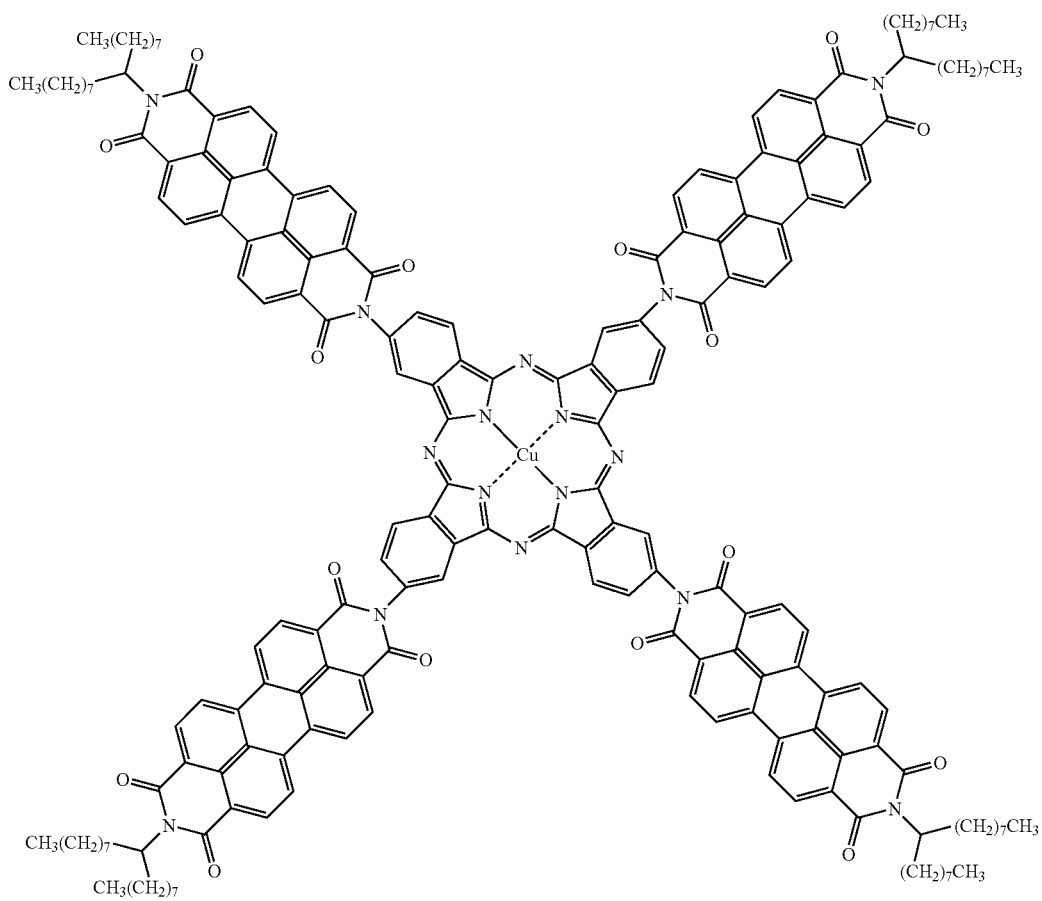
Exemplified compound 22

Synthetic Method

The organic semiconductor material of the present invention can be synthesized according to a known method. The following documents may be referred to: Chem. Soc. Rev., 2008, 37, 331 to 342; Helv. Chim. Act., 2005, 88, 1309 to 1343; Chem. Commun., 2004, 1564 to 1579; and the like. Examples of the method for synthesizing some of the exemplified compounds will be described below.

(Synthesis of Intermediate A)

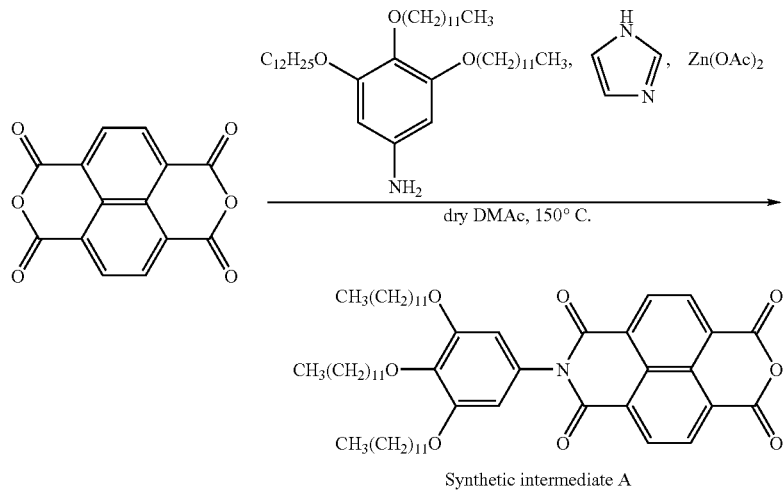

Synthetic intermediate A 3,4,5-tetradodecyloxyaniline, naphthalene-1,4,5,8-tetracarboxylic dianhydride (which is added in an amount larger than that of 3,4,5-tetradodecyloxyaniline by 10 or more equivalents), imidazole, zinc acetate, and dehydrated N,N-dimethylacetoamide (DMAc) are stirred at 150° C. in a nitrogen atmosphere, and then purified to yield a synthetic intermediate A.

(Synthesis of Exemplified Compound 2)

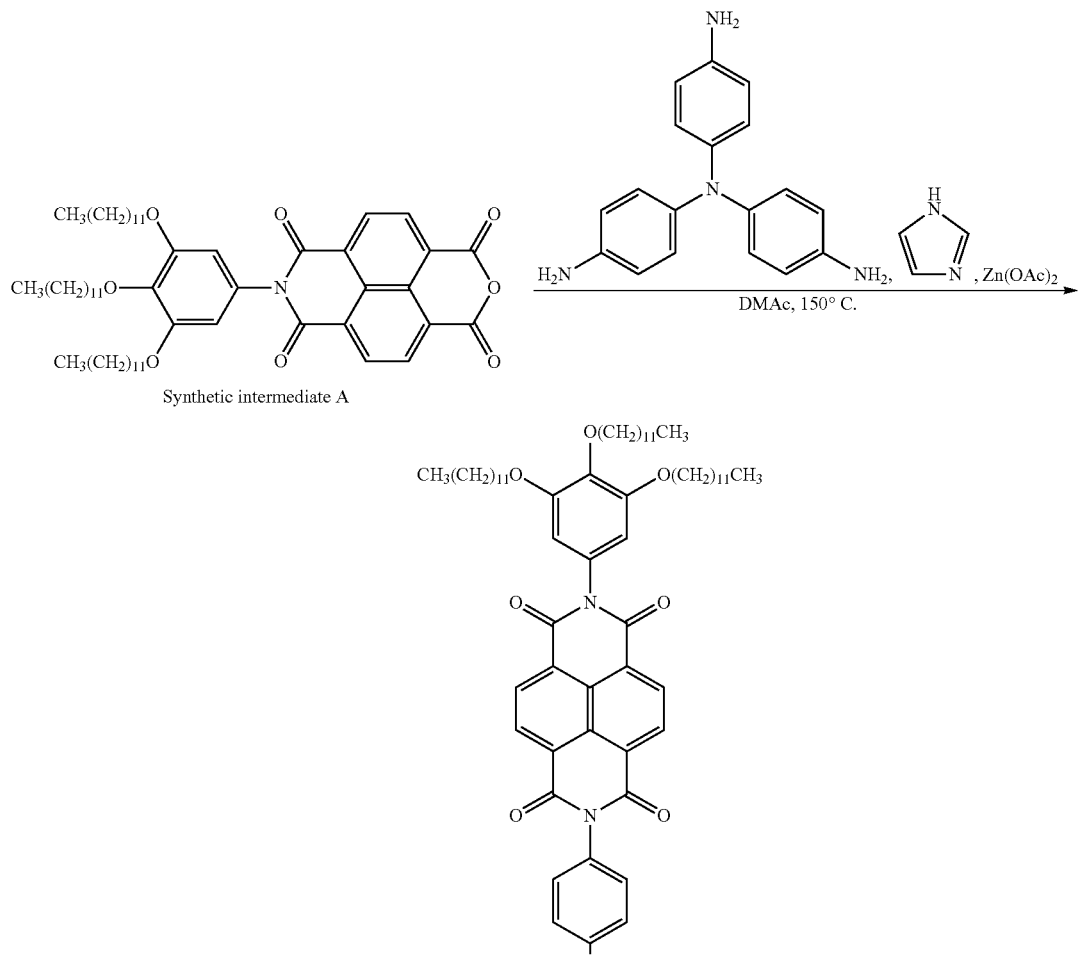

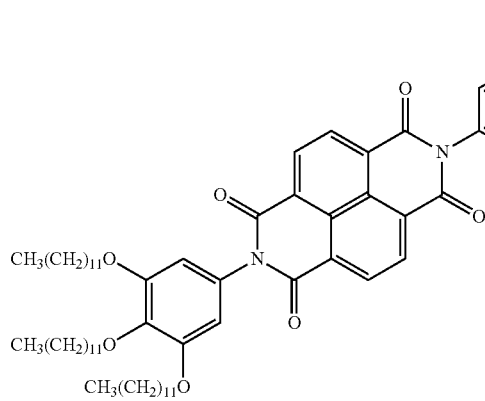

Exemplified compound 2

The synthetic intermediate A, tris(4-aminophenyl)amine, imidazole, zinc acetate, and dehydrated DMAc are stirred at 150° C. in a nitrogen atmosphere to yield the exemplified compound 2. In the same manner, the exemplified compounds 1 and 3 to 13 can also be synthesized.

(Synthetic Method of Synthetic Intermediate B)

1,7-dibromoperylene-3,4,9,10-tetracarboxylic anhydride, 3,4,5-tetradodecyloxyaniline (which is added in an amount larger than that of 1,7-dibromoperylene-3,4,9,10-tetracarboxylic anhydride by 2 or more equivalents), imidazole, zinc acetate, and dehydrated DMAc are stirred at 150° C. in a nitrogen atmosphere to yield a synthetic intermediate B.

(Synthetic Method of Synthetic Intermediate C)

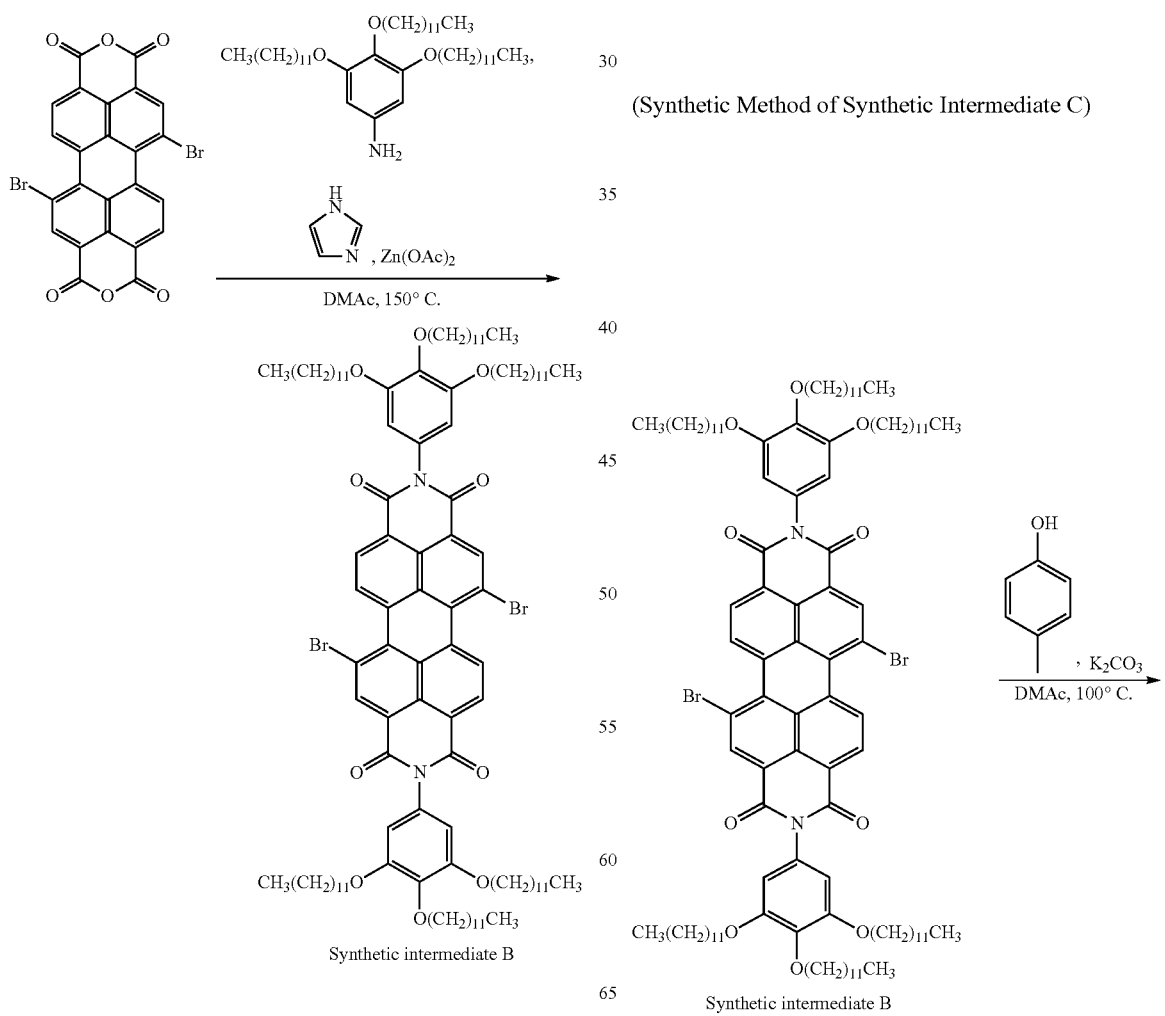

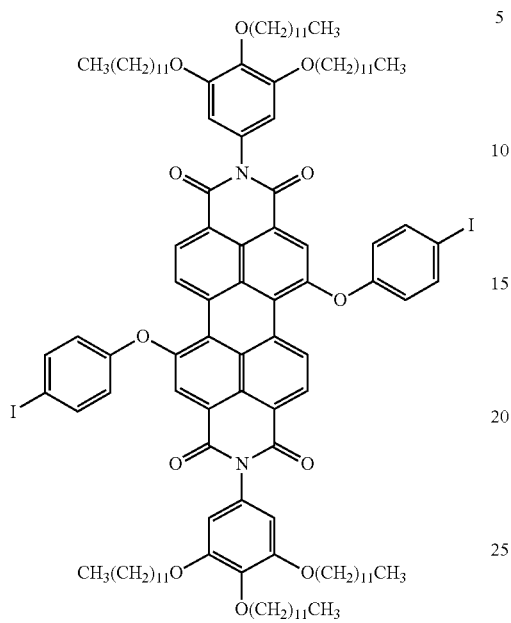
Synthetic intermediate C
The synthetic intermediate B, 4-iodophenol, potassium carbonate, and dehydrated DMAc are stirred at 120° C. to yield a synthetic intermediate C.
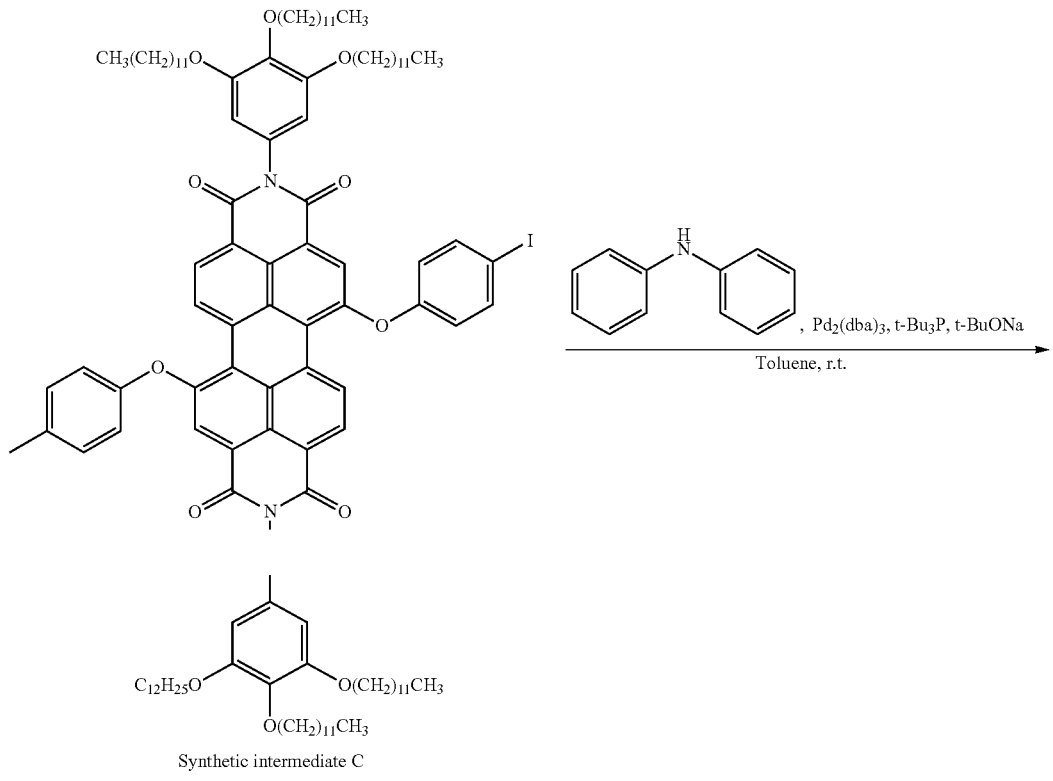
Synthetic intermediate C

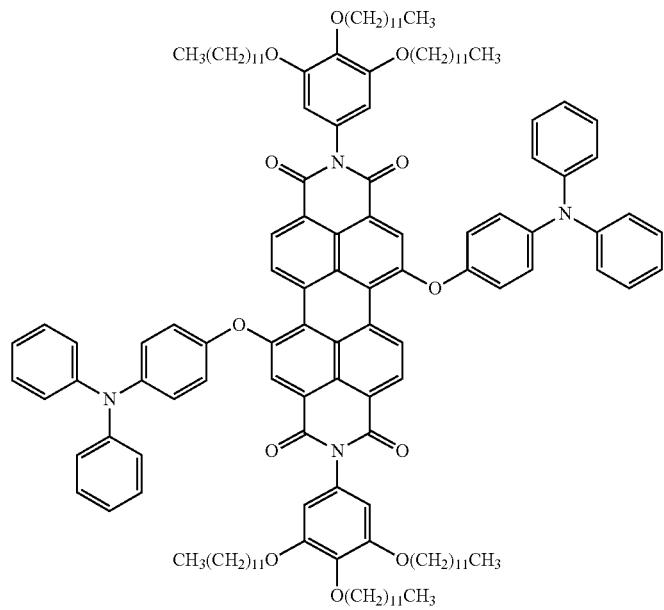
Exemplified compound 14
The synthetic intermediate C, N,N-diphenylamine, tris(dibenzylideneacetone)dipalladium, tri-tert-butylphosphine, sodium tert-butoxide, and toluene are stirred at room temperature to yield the exemplified compound 14. In the same manner, the exemplified compounds 15 to 17 can also be synthesized.
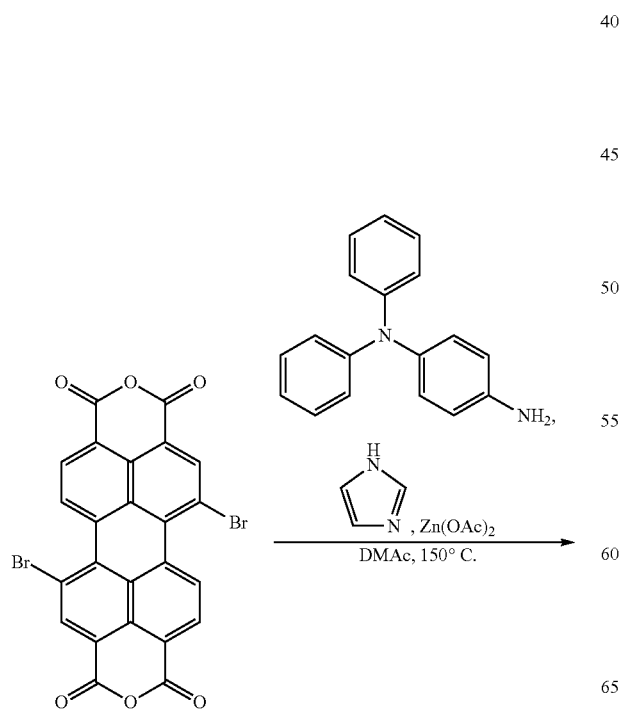
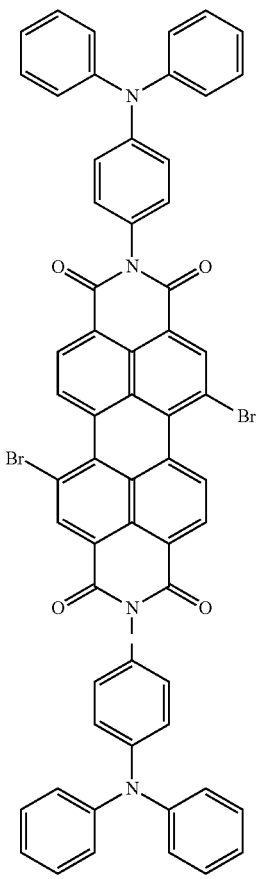
Synthetic intermediate D 1,7-dibromoperylene-3,4,9,10-tetracarboxylic anhydride, 4,4-diphenylbenzene-1,4-diamine, imidazole, zinc acetate, and dehydrated DMAc are stirred at 150° C. to yield a synthetic intermediate D.
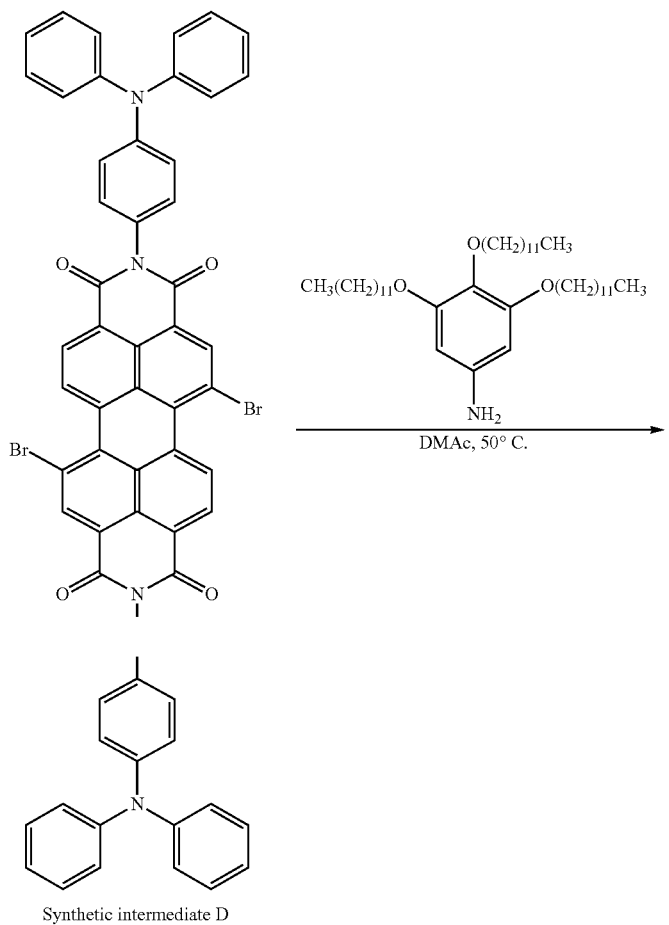
Synthetic intermediate D
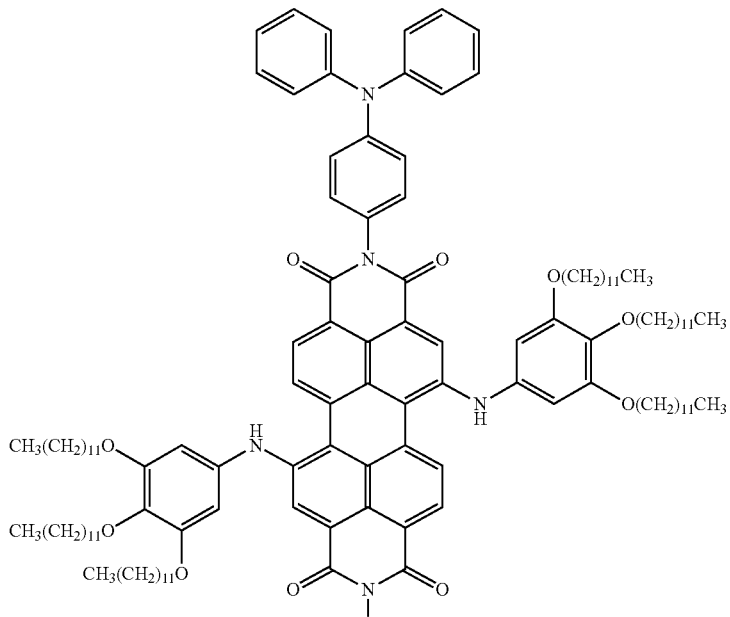

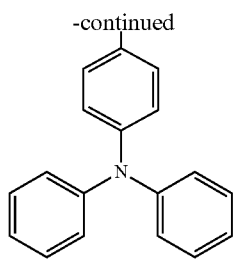

Exemplified compound 18

The synthetic intermediate D, 3,4,5-tetradodecyloxyaniline, and dehydrated DMAc are stirred at 50° C. to yield the exemplified compound 18. In the same manner, the exemplified compound 19 can also be synthesized.

The followings are heated and refluxed: 2,3,6,7-tetrabromo-1,4,5,8-naphtalenecarboxylic anhydride; 5-hexyl-5'-(4,4,5,5-tetramethyl-1,3,2-dioxaborane-2-yl)-2,2'-bithiophene; tetrakis(triphenylphosphine)palladium; sodium carbonate; toluene; methanol; and pure water. As a result, a synthetic intermediate E can be yielded.

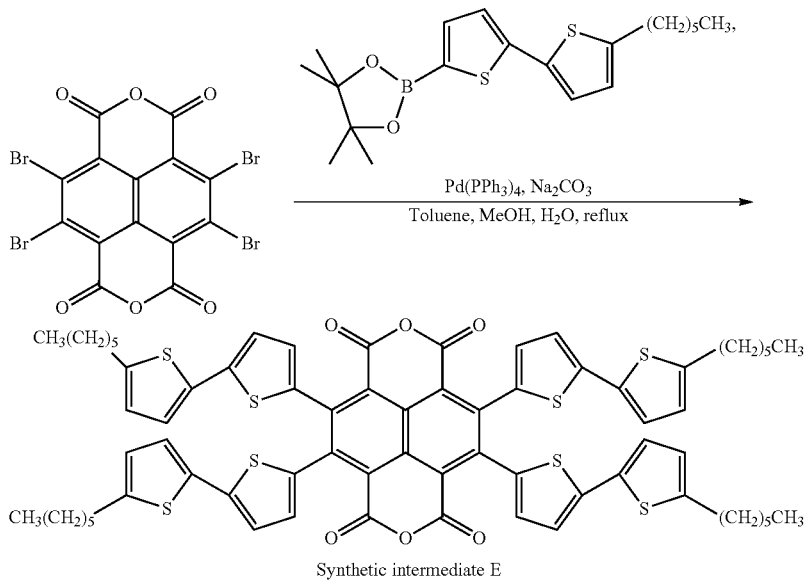

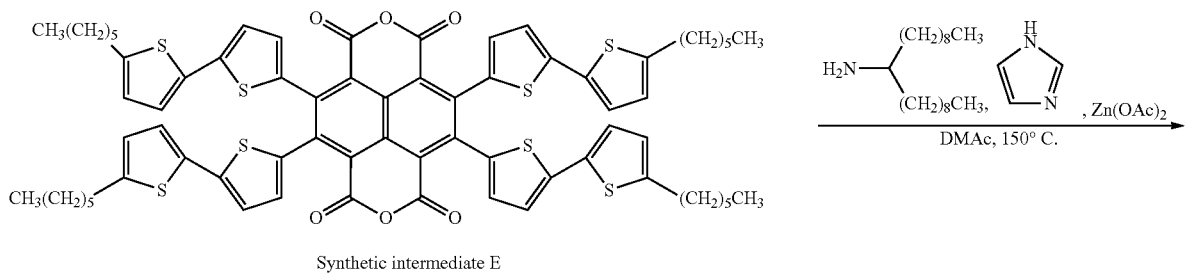

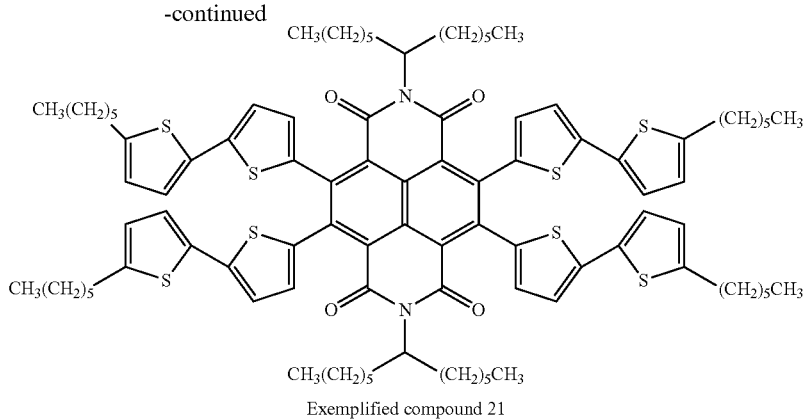
Exemplified compound 21
The synthetic intermediate E, 10-aminononadecane, imidazole, zinc acetate, and dehydrated DMAc are stirred at 150° C. to yield the exemplified compound 21. In the same manner, the exemplified compound 20 can also be synthesized.
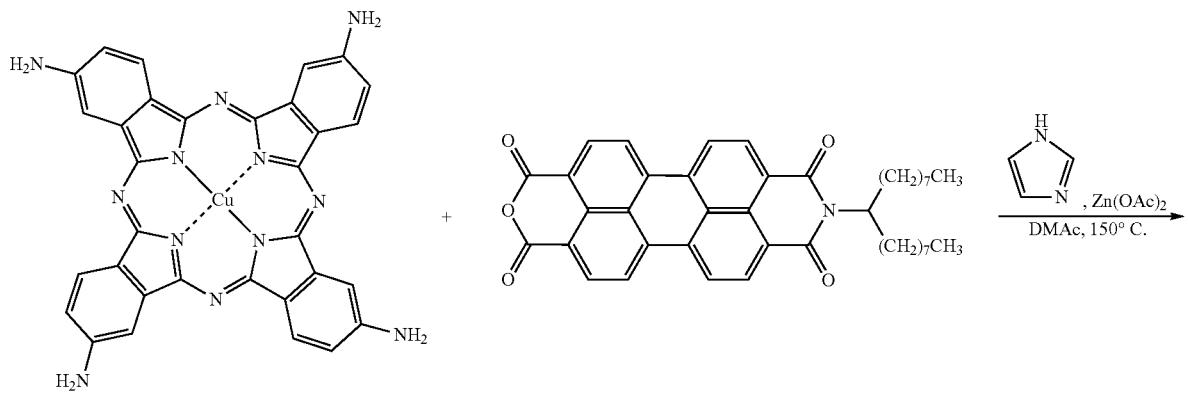
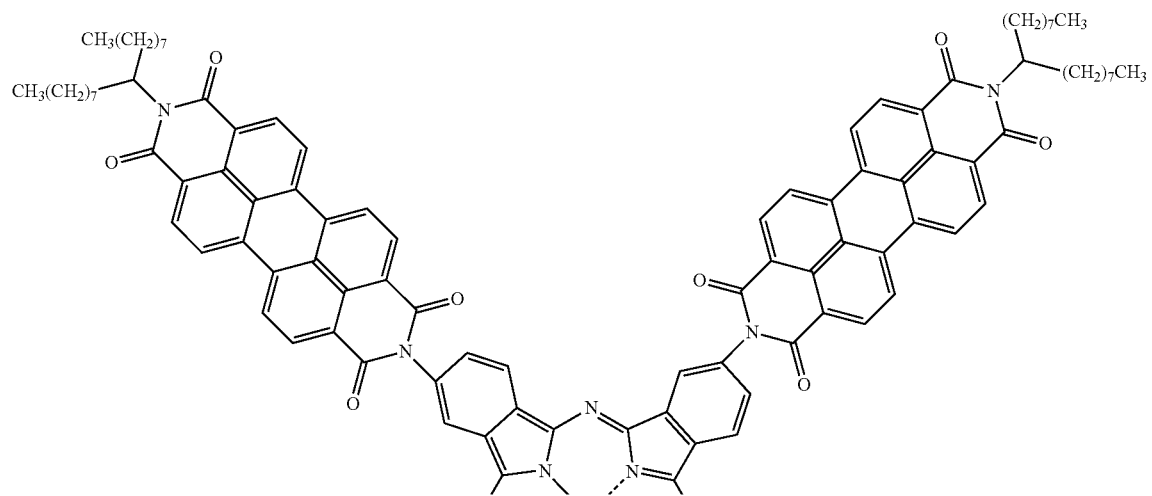

-continued

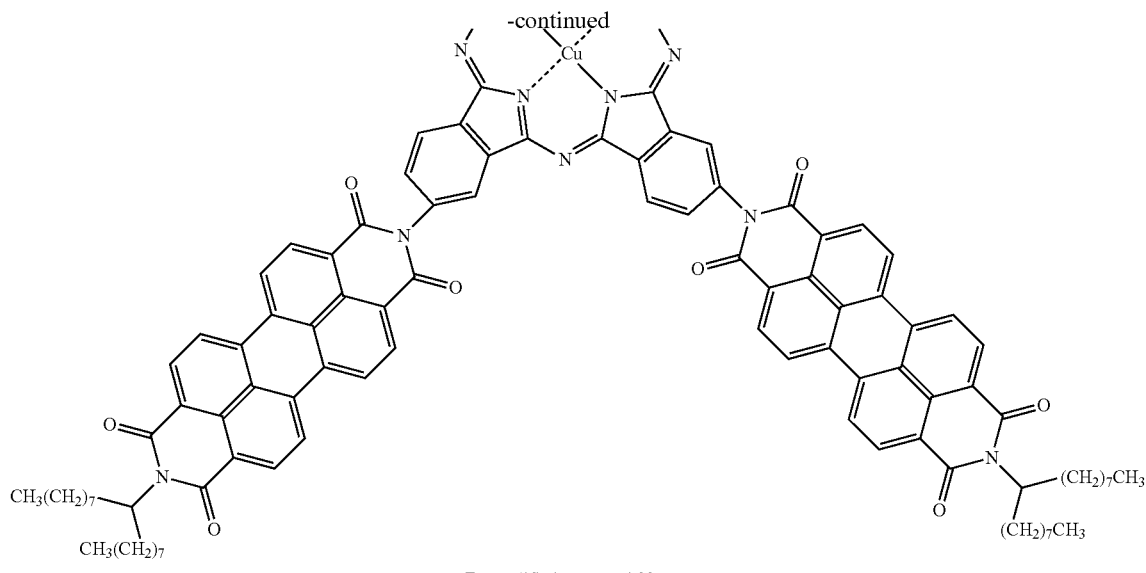

Exemplified compund 22

The followings are caused to react with each other at 150° C.: copper 4,4',4'',4'''-tetraaminophthalocyanine (J. Organomet. Chem., 2004, 21, 3357); N-(1-octylnonyl)perylene-3,4:9,10-tetracarboxylic acid-3,4-anhydride-9,10-imide (Chem. Eur. J., 1998, 4, 2110); imidazole; zinc acetate; and dehydrated DMAc. As a result, the exemplified compound 22 is yielded.

The liquid crystalline organic semiconductor material of the present invention can be preferably used for various kinds of an organic electronic device. The organic electronic device is not limited. However, it is preferably a device wherein an organic semiconductor thin film is used as an active layer. Examples of such an organic electronic device include an organic thin-film photoelectric conversion device, an organic thin-film transistor, an organic electroluminescence device, a gas sensor, an organic rectification device, an organic inverter, and an information recording device. The organic thin-film photoelectric conversion device may be used for a use of an energy conversion (organic thin-film solar cell) or for a use of an optical sensor (solid imaging device). The organic electronic device is preferably an organic thin-film transistor, an organic thin-film photoelectric conversion device, or an organic electroluminescence device, and furthermore preferably an organic thin-film transistor or an organic thin-film photoelectric conversion device.

The term "organic semiconductor material" in the present invention means an organic material exhibiting semiconductor characteristics. Similar to a material of an inorganic semiconductor, there are p-type organic semiconductor conducting positive holes as a carrier (hereinafter, also referred to as a "positive hole-transporting material") and n-type organic semiconductor conducting electrons as a carrier (hereinafter, also referred to as a "electron-transporting material").

The organic semiconductor material of the present invention is easily formed into a good-quality thin film. Thus, the organic semiconductor material is suitable for being used for a thin film. When the organic semiconductor material is formed into a thin film, it is also preferable that the organic semiconductor material is mixed with a binder material, another organic semiconductor material, or the like material to form the thin film. In this case, the amount of the organic semiconductor material of the invention in the film is preferably 1% by mass or more, more preferably 5% by mass or more, further more preferably 10% by mass or more. The film thickness is not particularly limited, but it is preferably from 1 nm to 100 µm, more preferably from 5 nm to 10 µm, further more preferably from 10 nm to 1 µm.

As a method of forming a thin film containing the organic semiconductor material of the present invention, there can be used any of a dry film forming process and a wet film forming process, preferably the wet film forming process. Specific examples of the dry film forming process include a physical vapor phase growth method such as a vacuum evaporation method, a spattering method, an ion plating method and a molecular beam epitaxy (MBE) method, and a chemical vapor deposition (CVD) method such as a plasma polymerization. As the wet film forming process (solution coating method), there is a method of dissolving an organic semiconductor material (organic photoelectric conversion material) in a solvent capable of dissolving the organic photoelectric conversion material or dispersing the photoelectric conversion material homogeneously, and making the resultant solution or dispersion a thin coating to form a film. As specific examples, there can be used a cast process, a blade coating process, a wire bar coating process, a splay coating process, a dip (an immersion) coating process, a bead coating process, an air knife coating process, a curtain coating process, an ink jet coating process, a spin coating process, and a Langmuir-Blodgett (LB) process. Preferably there can be used a cast process, a spin coating process and an ink jet coating process.

In the case where a thin film containing the organic semiconductor material of the present invention may be formed through a wet film forming process, the organic semiconductor material of the present invention or both said material and a binder resin are dissolved or dispersed in a proper organic solvent (e.g., hydrocarbons such as hexane, octane, decane, toluene, xylene, ethyl benzene, 1-methyl naphthalene and 1,2-dicyclobenzene; ketones such as acetone, methyl ethyl ketone, methyl isobutyl ketone and cyclohexanone; halogenated hydrocarbons such as dichloromethane, chloroform, tetrachloromethane, dichloroethane, trichloroethane, tetrachloroethane, chlorobenzene, dichlorobenzene, and chlorotoluene; esters such as ethyl acetate, butyl acetate, and amyl acetate; alcohols such as methanol, propanol, butanol, pentanol, hexanol, cyclohexanol, methylcellosolve, ethylcellosolve, and ethylene glycol; ethers such as dibutylether, tetrahydrofuran, dioxane, and anisole; polar solvents such as N,N-dimethylformamide, N,N-dimethylacetamide, 1-methyl-2-pyrrolidone, 1-methyl-2-imidazolidinone and dimethylsulfoxide) and/or water to prepare a coating liquid. A thin film can be formed using the thus-obtained coating liquid through various coating methods. A concentration of the organic semiconductor material (photoelectric conversion material) of the present invention in the coating liquid is preferably in the range of from 0.01 to 80% by mass, more preferably in the range of from 0.05 to 30% by mass, further more preferably in the range of from 0.1 to 10% by mass. Control of the concentration to such the range enables to form a film having arbitrary thickness. The thickness of the formed film can be measured with a probe-used thickness tester, an atomic force microscope (AFM), or the like.

In the case where a resin binder is used in the present invention, examples of the resin binder include insulating polymers such as polystylene, polycarbonate, polyarylate, polyester, polyamide, polyimide, polyurethane, polysiloxane, polysulfone, polymethylmethacrylate, polymethylacrylate, cellulose, polyethylene and polypropylene; and copolymers of these polymers; photoconductive polymers such as polyvinylcarbazol and polysilane, and electrically conductive polymers such as polythiophen, polypyrrole, polyaniline, and polypara phenylenevinilene. The resin binder may be used solely or, alternatively two or more kinds of the resin binder may be used in combination. Taking a mechanical strength of the thin film into consideration, preferred are resin binders having a high glass transition temperature. Whereas, taking a charge transfer degree into consideration, preferred are resin binders containing no polar group, photoconductive polymers and electrically conductive polymers. It is preferable in characteristics not to use such the resin binder. However, the resin binder is sometimes used according to the purpose. In this case, an amount of the resin binder used is not particularly limited, but preferably the binder is used in the range of from 0.1 to 90% by mass, more preferably in the range of from 0.1 to 50% by mass, and further preferably in the range of from 0.1 to 30% by mass, based on the thin film.

The film may be yielded by heating the organic semiconductor material up to the melting point thereof or higher without using any solvent to melt the material, and then cooling the organic semiconductor material. In this case, in order to prevent the organic semiconductor material from being thermally discomposed, it is preferable to conduct the heating in a vacuum or in an inert gas (such as nitrogen or argon).

When the film is formed on a substrate, the substrate may be heated or cooled. By varying the temperature of the substrate, the morphology of the film or the orientation/alignment of the molecule of the organic semiconductor material can be controlled. The temperature of the substrate is not particularly limited, but it is preferably from −200° C. to 300° C., more preferably from −100° C. to 250° C., further more preferably 0° C. to 200° C.

It is preferable that the orientation or the domain size of the liquid crystal or crystal of the organic semiconductor material is controlled. The controlling method therefor may be a method of applying an external stimulus such as heat, an electric field, a magnetic field, shearing force, or the like. It is preferable that the domain size is larger. It is most preferable that the whole of the film is made of a monodomain. In the case where the average domain size is sufficiently larger than the size between electrodes to be formed, substantially the same property as in the case of a monodomain is exhibited; thus, the case is similarly preferable. When the domain size is 1 μm or more, the domain size can be examined by observation with a polarizing microscope. In the present specification, the term "average domain size" means an average value of diameters of circles having areas equivalent to areas of pattern units of a liquid crystal or crystal texture observed with a polarizing microscope. The preferable domain size is depend on the size between electrodes of a device, but it is preferably 10 nm or more, more preferably 100 nm or more, further more preferably 1 μm or more.

In order to control the orientation/alignment of the molecule of the organic semiconductor material, it is also preferable to provide an orientation/alignment controlling layer on a surface of the substrate. The orientation/alignment controlling layer is not particularly limited. It includes, for example, a polyimide film subjected to rubbing treatment, a self-assembled monolayer (SAM), or an organic vapor-deposited film the orientation of which is controlled.

The following will describe, in detail, the structure of an organic thin-film transistor element using the organic semiconductor material of the invention (hereinafter referred to as the "organic thin-film transistor element of the invention").

FIG. 2 is a sectional view that schematically illustrates the structure of a typical organic thin-film transistor element using the organic semiconductor material of the invention. The organic thin-film transistor element of the invention may have any structure, and most preferably has a field effect transistor (FET) structure as illustrated in FIG. 2. This transistor has a laminated structure as its basic structure. As the lowest layer thereof, a substrate 11 is arranged, an example thereof being a polyester film such as a polyethylene naphthoate (PEN) film or polyethylene terephthalate (PET) film, a polyimide film, a ceramic, a silicon, a quartz or a glass. A gate electrode 12 is arranged on a partial region of the upper surface of the substrate 11, and further an insulator layer 13 is laid to cover the electrode and further contact the substrate in its region other than its electrode-covered region. Furthermore, a semiconductor active layer 14 containing the organic semiconductor material of the invention is laid on the upper surface of the insulator layer 13, and a source electrode 15a and a drain electrode 15b are arranged on partial regions of the upper surface of the layer 14, so as to be separated from each other. The constituting materials of the electrode 12 and the electrodes 15a and 15b are not particularly limited as far as the materials exhibit electroconductivity. Thus, the materials may each be a known electroconductive material, for example, a metallic material such as Cr, Al, Ta, Mo, Nb, Cu, Ag, Au, Pt, Pd, In, Ni or Nd, any alloy material thereof, a carbon material, an electroconductive polymer, or a charge transfer complex. A buffer layer (not illustrated in FIG. 2) may be arranged between the semiconductor active layer and the electrodes 15a and/or 15b to attain a decrease in damage of the semiconductor active layer when the films for electrode material are formed, a decrease in contact resistance of the interface between the semiconductor active layer and the electrodes, or some other purposes. The structure shown in FIG. 2 is called as a top contact type device. Besides, preferably used are bottom contact type device in which the two electrodes 15a and 15b are arranged at the bottom portion of the organic semiconductor layer. The organic thin-film transistor element of the invention may have a vertical transistor structure, wherein carries flow along the film thickness direction of an organic semiconductor film.

The gate width (channel width) W and gate length (channel length) L are not particularly limited, but the ratio of W to L is preferably 10 or more, and more preferably 20 or more.

There is no particular limitation to the thickness of each layer. However, if thinner transistors are required, for example, a whole thickness of the transistor is preferably controlled to the range of from 0.1 to 0.5 μm. For achieving such the thickness control, a thickness of each layer is preferably controlled to the range of from 10 to 400 nm, whereas a thickness of electrode is preferably controlled to the range of from 10 to 50 nm.

Though, there is no particular limitation to the material constituting an insulator layer as long as required insulating effect is obtained, examples thereof include silicon dioxide, silicon nitride, polyester insulating materials, polycarbonate insulating materials, acrylic polymer-based insulating materials, epoxy resin-based insulating materials, polyimide insulating material, and polyparaxylylene resin-based insulating materials.

In order to make the storability of the element high, it is preferable to enclose the element air-tightly to keep an inert atmosphere around the element. The material for the enclosing is preferably an inorganic material such as metal, glass, silicon nitride or alumina, or a polymeric material such as parylyne. When the element is enclosed, a drying agent or the like may be enclosed.

The organic semiconductor material of the invention may be used as a p-type organic transistor material, an n-type organic transistor material, or an ambipolar transistor material.

The following will describe, in detail, the structure of an organic thin-film photoelectric conversion device using the organic semiconductor material of the invention (hereinafter referred to as the "organic thin-film photoelectric conversion device of the invention").

FIG. 3 is a sectional view that schematically illustrates the structure of a typical organic thin-film photoelectric conversion device using the organic semiconductor material of the invention. The element in FIG. 3 has a laminated structure. As the lowest layer thereof, a substrate 21 is arranged, and an electrode layer 22 is laid on the upper surface thereof. A photoelectric conversion layer (semiconductor active layer) 23 containing the organic semiconductor material of the invention is further laid as the upper surface thereof. Furthermore, an electrode layer 24 is laid on the upper surface thereof. This structure may contain, between the electrode layer 22 or 24 and the photoelectric conversion layer 23, a buffer layer for making the smoothness of the surface high, a carrier injecting layer for promoting the injection of holes or electrons from the electrodes, a carrier transporting layer for transporting holes or electrons, a carrier blocking layer for blocking holes or electrons, and/or some other layer (a layer may function as two or more of these layers), the layers being not illustrated in FIG. 3. In the invention, the layer(s) arranged between the electrode layer and the photoelectric conversion layer is/are (each) expressed by the wording "buffer layer" regardless of the function of the layer. It is not necessarily required that the electrodes and the individual layers are each a flat plane. Thus, the layers may each have large convexes and concaves, or have a three-dimensional shape (such as a comb shape).

The material used for the substrate 21 is not particularly limited as far as the material is a material which transmits visible rays or infrared rays. The transmittance thereof in visible rays or infrared rays is preferably 60% or more, more preferably 80% or more, even more preferably 90% or more. Examples of the material include a polyester such as polyethylene naphthalate (PEN) or polyethylene terephthalate (PET), polyimide, ceramic, silicon, quartz and glass. The thickness of the substrate is not particularly limited.

The material used for the electrode layer 22 is not particularly limited as far as the material is a material which transmits visible rays or infrared rays and further exhibits electroconductivity. The transmittance thereof in visible rays or infrared rays is preferably 60% or more, more preferably 80% or more, even more preferably 90% or more. Examples of the material include transparent electroconductive oxides such as ITO, IZO, $SnO_2$, ATO (antimony doped tin oxide), ZnO, AZO (Al doped zinc oxide), GZO (gallium doped zinc oxide), $TiO_2$, and FTO (fluorine doped tin oxide). From the viewpoint of process adaptability and smoothness, ITO or IZO is particularly preferable. The film thickness is not particularly limited, and is preferably from 1 to 200 nm, more preferably from 5 to 100 nm. When the electrode 12 has structural independency, the substrate 21 is not necessarily essential. When the electrode 22 functions also as the substrate 21, the film thickness may be larger than the above-mentioned thickness range.

The photoelectric conversion layer 23 contains the organic semiconductor material of the invention. The layer 23 may be a monolayer made of the organic semiconductor material of the invention, or a layer having a laminate structure composed of such a monolayer and a layer containing a different semiconductor material (in this case, the laminating order of the layers or the number of the laminated layers may be selected at will). The layer 23 may be a layer containing both of the organic semiconductor material of the invention and a different semiconductor material (in this case, the two may be completely mixed with each other at a molecular level, or may form some phase-separation structure). When the material of the invention is used in combination with a different semiconductor material, it is preferable to use a combination of the material of the invention with an n-type semiconductor material in order to compensate for electron transporting power since organic semiconductor materials are generally lower in electron transporting property than in hole transporting property in many cases.

The n-type semiconductor material used in the invention may be any one of organic semiconductor materials and inorganic semiconductor materials as far as the material has electron transporting property. The material is preferably a fullerene compound, an electron-deficient phthalocyanine, a naphthalenetetracarbonyl compound, a perylenetetracarbonyl compound, a TCNQ analogue, or an inorganic semiconductor, more preferably a fullerene compound, a phthalocyanine, a naphthalenetetracarbonyl compound, or a perylenetetracarbonyl compound, in particular preferably a fullerene compound. In the invention, the wording "fullerene compound" denotes a substituted or unsubstituted fullerene. The fullerene may be any one of $C_{60}$, $C_{70}$, $C_{76}$, $C_{78}$, $C_{80}$, $C_{82}$, $C_{84}$, $C_{86}$, $C_{88}$, $C_{90}$, $C_{96}$, $C_{116}$, $C_{180}$, $C_{240}$, $C_{540}$, and others. The fullerene is preferably substituted or unsubstituted $C_{60}$, $C_{70}$, or $C_{86}$, and is in particular preferably PCBM ([6,6]-phenyl-$C_{61}$-methyl butyrate) or an analogue thereof (such as a compound wherein the $C_{60}$ moiety is replaced into $C_{70}$, $C_{86}$ or the like, a compound wherein the benzene ring as a substituent is replaced into a different aromatic ring or a hetero ring, or a compound wherein the methyl ester is replaced into a n-butyl ester an i-butyl ester or the like). The wording "electron-deficient phthalocyanine" denotes a phthalocyanine to which 4 or more electron-withdrawing groups are bonded, or an analogues thereof; or an electron-deficient phthalocyanine analogue. The phthalocyanine analogue may be tetrapyrazino porphyrazine, naphthalocyanine, anthracyanine or the like (such as $F_{16}MPc$ or FPc-S8) besides any metal phthalocyanine. The naphthalenetetracarbonyl compound is not particularly limited, and is preferably naphthalenetetracarboxylic anhydride (NTCDA), a naphthalenebisimide compound (NTCDI), a perynone pigment (such as Pigment Orange 43 or Pigment Red 194), or the like. The perylenetetracarbonyl compound is not particularly limited, and is preferably perylenetetracarboxylic anhydride (PTCDA), a perylenebisimide compound (PTCDI), or a benzimidazole condensed ring compound (PV). The TCNQ analogue is TCNQ or a compound wherein one or two of the benzene ring moieties of TCNQ is/are (each) replaced into a different aromatic ring or a hetero ring. The TCNQ analogue is, for example, TCNQ, TCAQ, or TCN3T. The inorganic semiconductor is not particularly limited as far as the semiconductor has electron transporting property. Examples thereof include $TiO_2$, $TiSrO_3$, $ZnQ$, $Nb_2O_3$, $SnO_2$, $WO_3$, Si, CdS, CdSe, $V_2O_5$, ZnS, ZnSe, SnSe, $KTaO_3$, $FeS_2$, PbS, hiP, GaAs, $CuInS_2$ and $CuInSe_2$. Particularly preferable examples of the n-type organic semiconductor material are as follows.

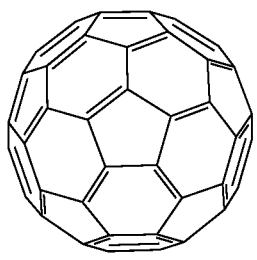

$C_{60}$

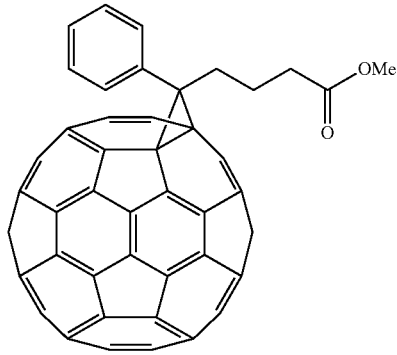

PCBM

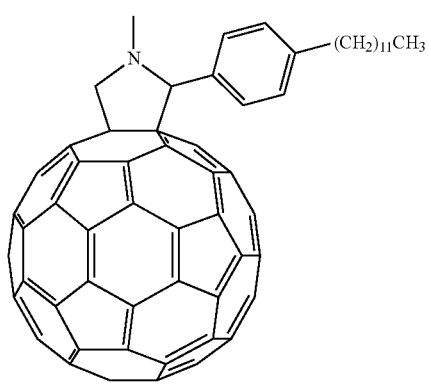

C60MC12

-continued

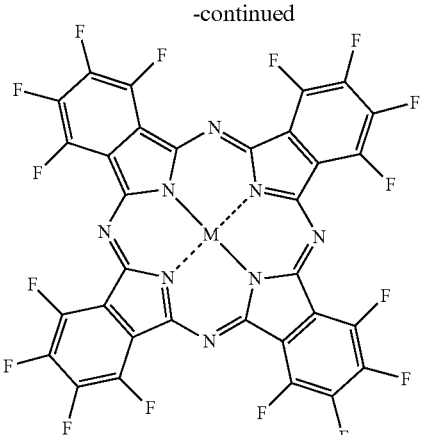

$F_{16}MPc$

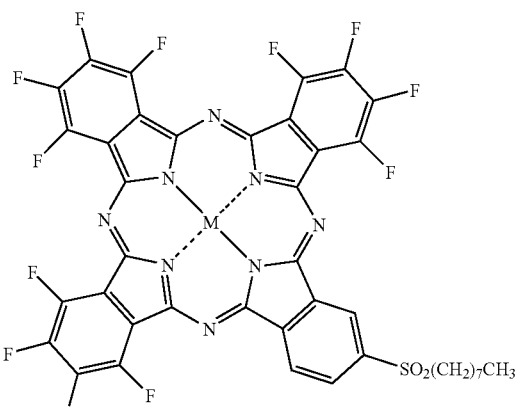

FPc-S8

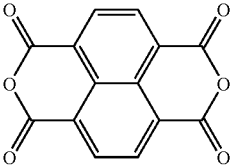

NTCDA

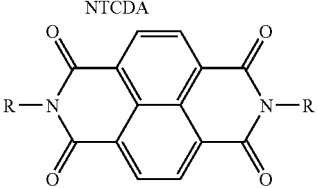

NTCDI

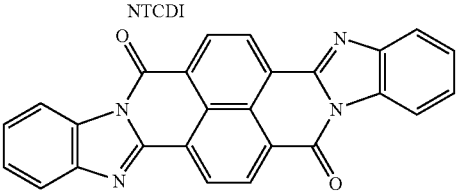

PO43

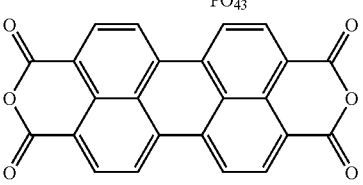

PTCDA

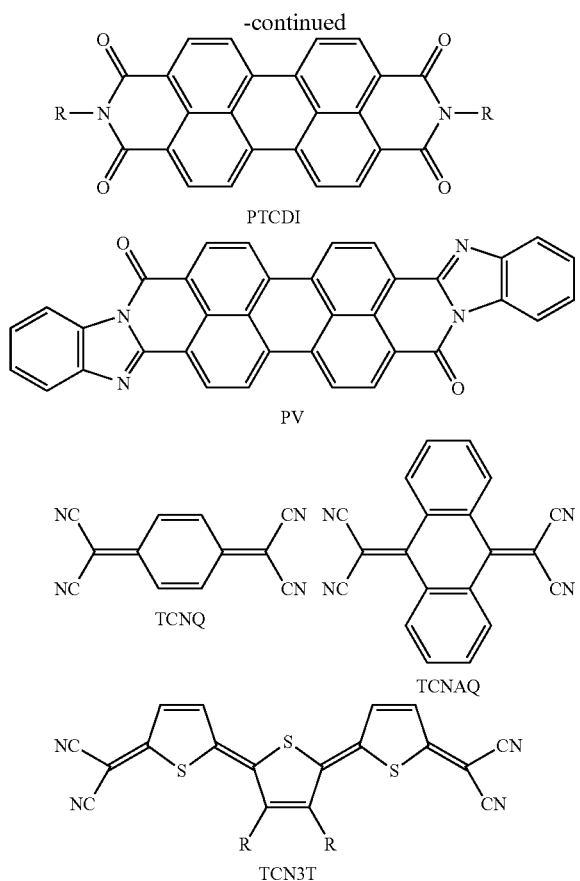

The material used for the buffer layer may be any organic material or inorganic material as far as the material is a material having a capability of transporting carriers. The material is preferably amorphous. The buffer material having hole transporting property may be any material, and is preferably an electroconductive polymer (such as PEDOT:PSS), a triarylamine compound (such as m-MTDATA), an inorganic semiconductor material (such as $Si_{1-x}C_x$ wherein $0 \leq X \leq 1$), CuI, CuS, GaAs, ZnTe, $Cu_2O$, $Cu_2S$, CuSCN, CuF, CuCl, CuBr, $CuInSe_2$, $CuInS_2$, $CuAlSe_2$, $CuGaSe_2$, $CuGaS_2$, GaP, NiO, CoO, FeO, $Bi_2O_3$, $MoO_2$, $Cr_2O_3$, or some other inorganic oxide. The buffer material having electron transporting property may be any material, and is preferably a metal complex compound (such as Alq), Bathocuproin, an inorganic fluoride (such as LiF or $CaF_2$), an inorganic oxide (such as SiOx, TiOx or ZnO), an electroconductive polymer (such as poly-p-phenylenevinylene having cyano groups (CN-PPV) or perynone polymer (BBL) as well as any one of the materials described above as an n-type semiconductor material, and is more preferably a naphthalene compound, Bathocuproin, an inorganic fluoride or an inorganic oxide.

The material used for the electrode layer 14 is not particularly limited as far as the material exhibits electroconductivity. In order to make the light-utilization efficiency of the element high, the material is a material high in light reflectivity. The material is preferably Al, Pt, W, Au, Ag, Ta, Cu, Cr, Mo, Ti, Ni, Pd or Zn, and is more preferably Al, Pt, Au or Ag. The film thickness of the electrode layer 14 is not particularly limited, and is preferably from 1 nm to 1 μm, more preferably from 5 nm to 500 nm.

In order to make the storability of the element high, it is preferable to enclose the element air-tightly to keep an inert atmosphere around the element. The material for the enclosing is preferably an inorganic material such as metal, glass, silicon nitride or alumina, or a polymeric material such as parylyne. When the element is enclosed, a drying agent or the like may be enclosed.

The organic thin-film photoelectric conversion device of the invention may be used for an energy converting application (organic thin-film solar cell) or for an optical sensor (solid imaging device). When the conversion device of the invention is used for an energy converting application, the organic thin-film photoelectric conversion device of the invention may be used alone or may be used in a tandem form of the conversion device and a different thin-film photoelectric conversion device. The method for producing a tandem form is detailed in Applied Physics Letters, 2004, 85, 5757 to 5759, and the document can be referred to. When the conversion device is used as an optical sensor, it is preferred, for improving the S/N ratio, to apply a bias to the electrodes 12 and 14 across these electrodes so as to read signals. In this case, the bias applied to the photoelectric conversion layer is preferably $1.0 \times 10^5$ V/cm or more and $1.0 \times 10^7$ V/cm or less. Solid imaging devices using an organic thin-film photoelectric conversion device are detailed in JP-A-2003-234460, JP-A-2003-332551, JP-A-2005-268609, or the like, and the documents can be referred to.

According to the invention, a novel liquid crystalline organic semiconductor material is provided wherein the property of transporting two carrier species (holes and electrons) and photoelectric conversion property are exhibited by the component alone. When this organic semiconductor material is used, various organic electron devices (in particular, an organic thin-film transistor and an organic thin-film photoelectric conversion device) excellent in characteristics can be obtained.

The present invention will be described in more detail based on the following examples, but the invention is not intended to be limited thereto.

EXAMPLES

Examples of Synthesis

Example of Synthetic Example A

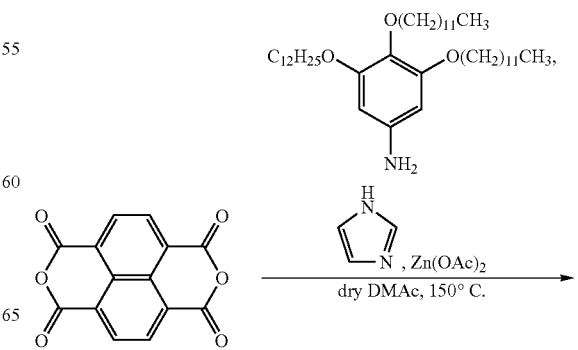

-continued

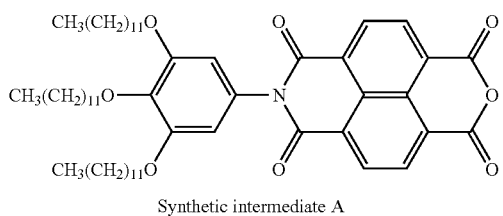

Synthetic intermediate A

The following were stirred at 150° C. for 4 hours in a nitrogen atmosphere: naphthalene-1,4,5,8-tetracarboxylic dianhydride (4.16 g, 15.5 mmol); 3,4,5-tetradodecyloxyaniline (1.00 g, 1.55 mmol); imidazole (2.11 g, 31.0 mmol); zinc acetate (568 mg, 3.10 mmol); and dehydrated N,N-dimethylacetoamide (DMAC) (50 mL). The resultant was cooled to room temperature, and then 100 mL of pure water was added thereto. The resultant was filtrated, and the resultant precipitate was washed with pure water, 5% hydrochloric acid and methanol successively. Next, the precipitate was put into 50 mL of acetic anhydride, and the solution was boiled for 1 hour. The resultant was then filtrated, and the resultant precipitate was washed with methanol and acetone successively. The precipitate was dissolved into 50 mL of chloroform, and then insolubles are filtrated off. A precipitate was caused to be generated again with 300 mL of methanol. The precipitate was collected by filtration, and vacuum-dried to yield synthetic intermediate A (700 mg, 0.781 mmol, 51%).

$^1$H-NMR (300 MHz, CDCl$_3$) δ=8.863 (s, 4H), 6.476 (s, 2H), 4.037 (t, 2H), 3.946 (t, 4H), 1.880 to 1.180 (m, 60H), 0.920 to 0.800 ppm (m, 9H).

(Synthesis of Exemplified Compound 2)

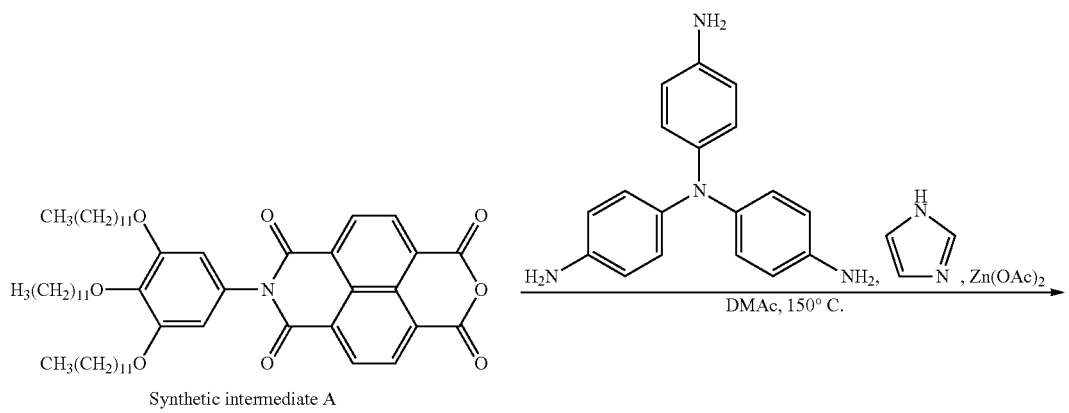

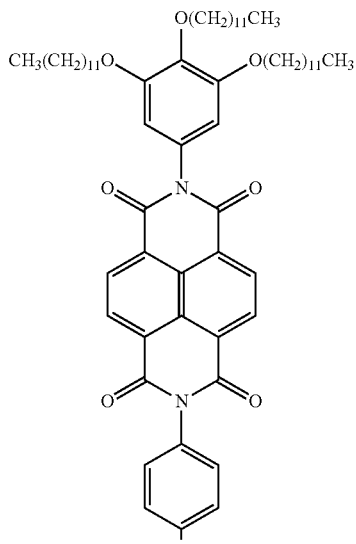

-continued

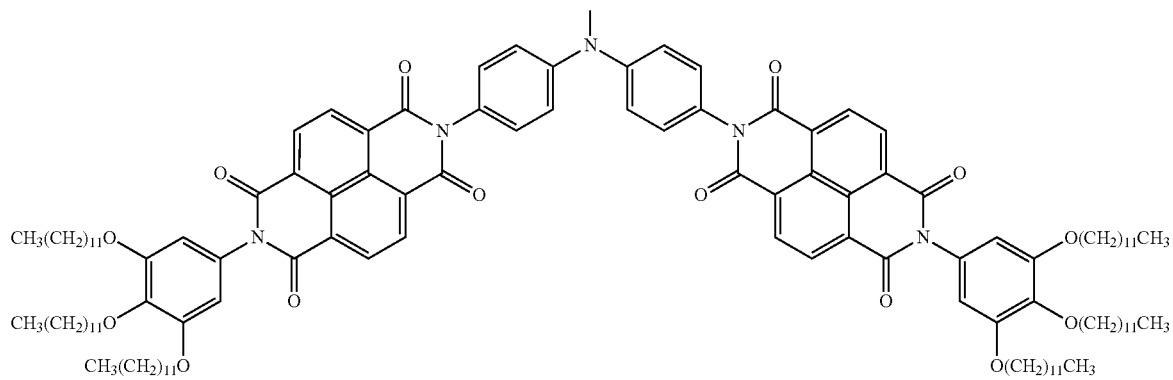

Exemplified compound 2

In a nitrogen atmosphere, the synthetic intermediate A (430 mg, 0.480 mmol), tris(4-aminophenyl)amine (42.1 mg, 0.145 mmol), imidazole (39.5 mg, 0.580 mmol), zinc acetate (26.6 mg, 0.145 mmol), and dehydrated N,N-dimethylacetoamide (5 mL) were heated at 150° C. for 5 hours. The resultant was cooled to room temperature, and then 50 mL of 5% hydrochloric acid was added thereto. The resultant was filtrated, and then the resultant precipitate was washed with pure water, methanol, acetone, ethyl acetate, and hexane successively to yield exemplified compound 2 (415 mg, 0.142 mmol, 98%).

$^1$H-NMR (300 MHz, CDCl$_3$) δ=8.862 (s, 12H), 7.506 (d, 6H), 7.315 (d, 6H), 6.515 (s, 6H), 4.046 (t, 6H), 3.958 (t, 12H), 1.860 to 1.116 (m, 180H), 0.993 to 0.788ppm (m, 27H)

$λ_{max}$ (CHCl$_3$)=380 nm (ε=1.0×10$^5$), 360 nm (ε=9.1×10$^4$), 343 nm (ε=6.4×10$^4$), 307 nm (ε=3.8×10$^4$), 220 nm (ε=1.2×10$^5$)

$E^{Ox}$=+0.42V (vs Ag/AgCl in CH$_3$CN), +0.75V (vs Ag/AgCl in CH$_3$CN)

$E^{Red}$=−0.80V (vs Ag/AgCl in CH$_3$CN)

The exemplified compound 1 is a compound where the following were linked to each other through a single bond: a triphenylamine residue (it is known according to Chem. Mater., 2007, 107, 953-1010 and others that the residue exhibits a hole mobility of 10$^{-5}$ cm$^2$/Vs or more), which is a p-type organic semiconductor compound residue, and a naphthalenebisimide residue (it is known according to Nature, 2000, 404, 478-481 and others that the residue exhibits an electron mobility of 10$^{-5}$ cm$^2$/Vs or more), which is an n-type organic semiconductor compound residue.

Example 1

(Liquid Crystallinity)

Figure 4:
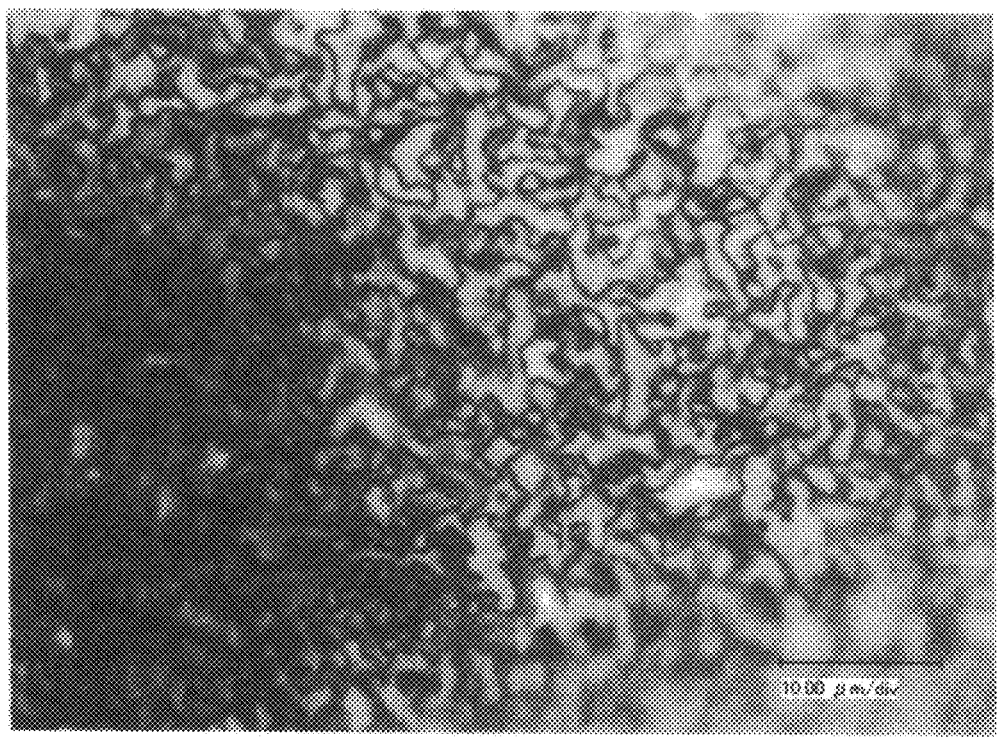
FIG. 4 is a polarizing microscopic photograph of the exemplified compound 2, which is a liquid crystalline organic semiconductor material of present the invention.

The exemplified compound 2 was heated to 300° C. on a quartz substrate, and then cooled to room temperature. A polarizing microscope was used to observe the compound under a cross nicol condition. As a result, a texture as shown in FIG. 4 was observed. From this fact, it was ascertained that the exemplified compound 2 exhibited liquid crystallinity at room temperature.

The exemplified compound 2 was measured by DSC and observed with the polarizing microscope. As a result, it was observed that the compound was changed from a liquid crystal phase to an isotropic liquid crystal phase at about 252° C. when the compound was heated.

Example for Comparison 1

The liquid crystallinity of compound for comparison 1 described in J. Mater. Chem., 2006, 16, 874-884 was examined by DSC analysis and observed with a polarizing microscope. However, the compound did not exhibit liquid crystallinity.

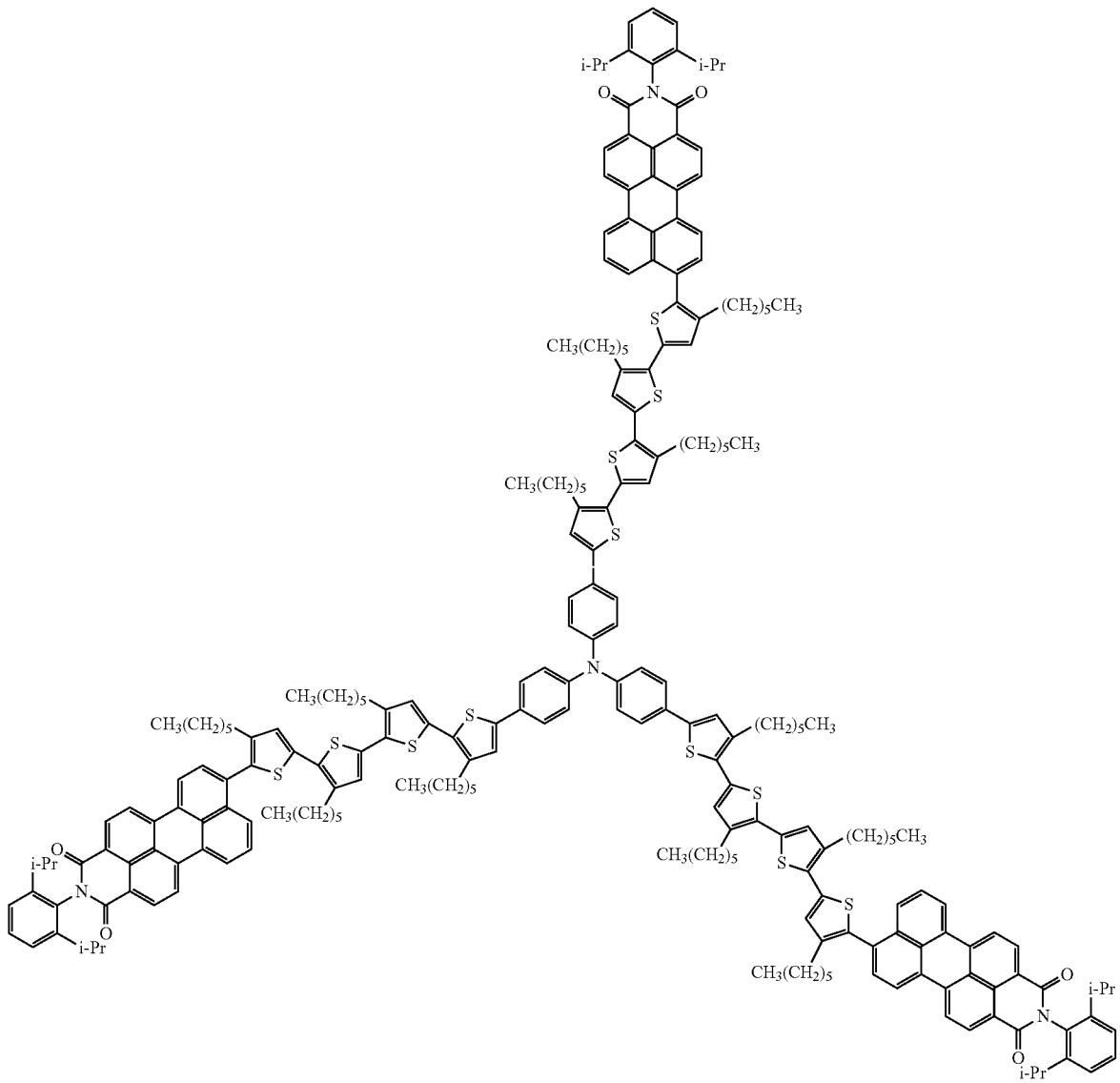

Compound for comparison 1

Example 2

(Characteristic of Organic Thin-Film Transistor)

Figure 5:
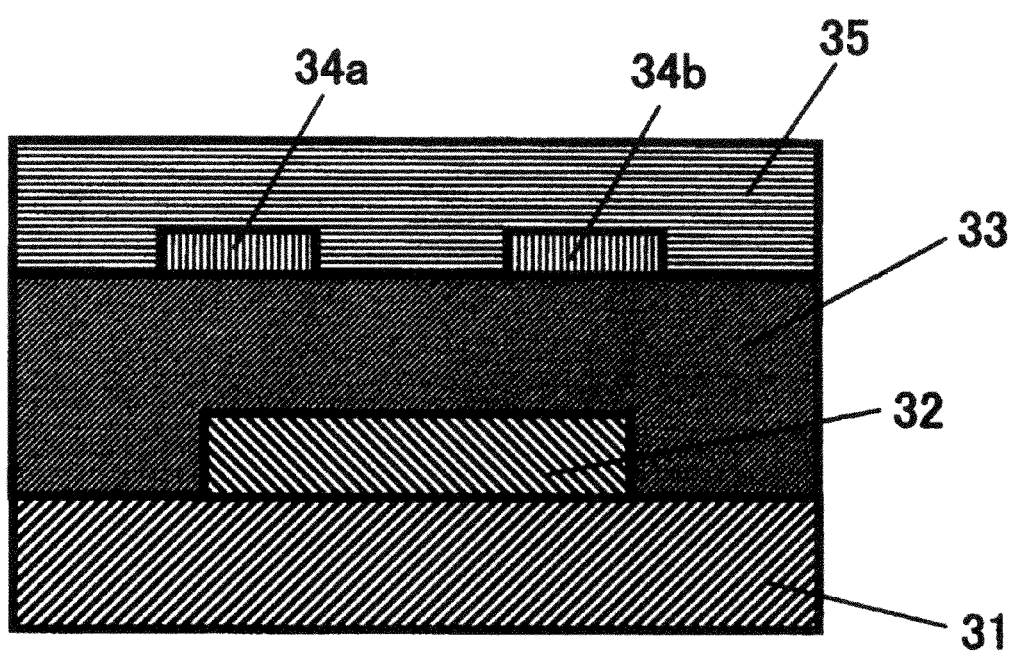
FIG. 5 is a sectional view which schematically illustrates a substrate for measuring an organic thin-film transistor characteristic, used in the present invention.
Figure 6A:
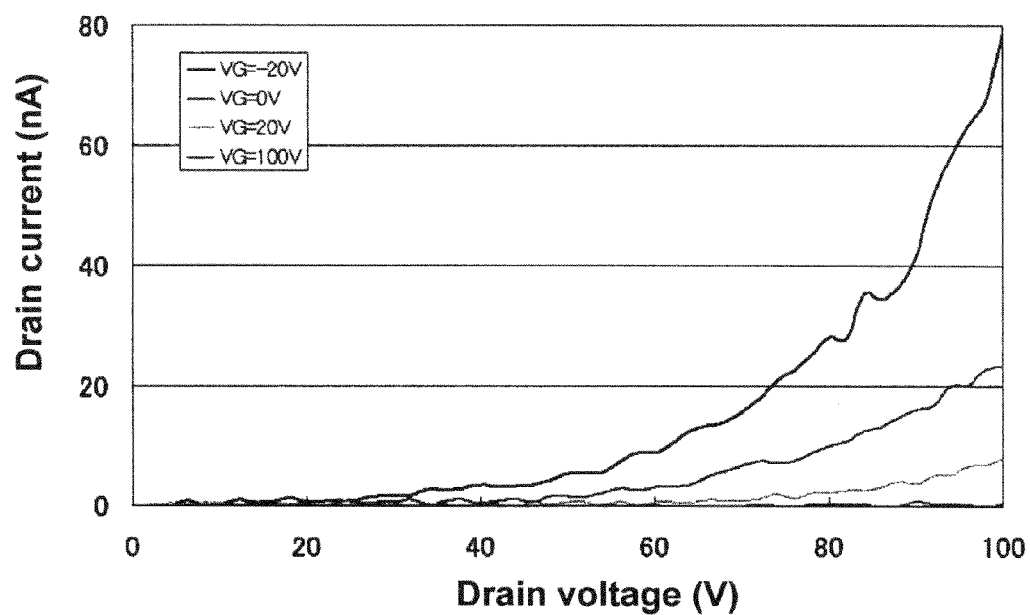
FIGS. 6(a) and 6(b) each are a chart showing the characteristic of an organic thin-film transistor device using the exemplified compound 2, which is a liquid crystalline organic semiconductor material of the present invention, and specifically
Figure 6B:
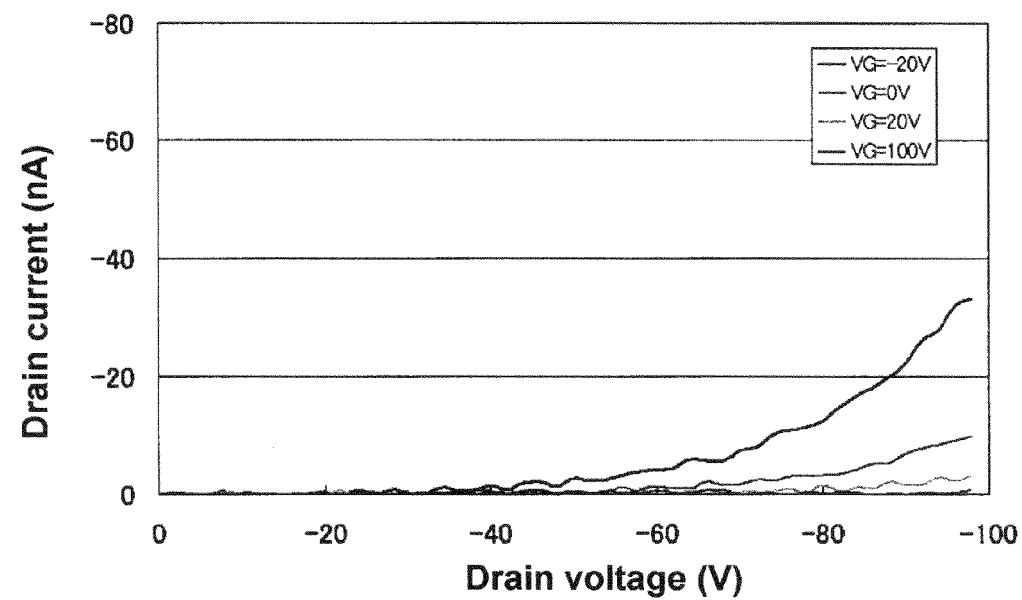

The exemplified compound 2 (1 mg) was dissolved into chloroform (1 mL), and the solution was drop-cast onto a FET-property-measuring substrate to yield a FET-property-measuring sample having an even thickness of 500 nm or less. The used FET-property-measuring substrate was a bottom-contact type substrate (its source and drain electrodes were each made of chromium/gold arranged in a comb form (gate width W=100000 μm, and gate length L=100 μm)) illustrated schematically in FIG. 5; its insulator film was made of $SiO_2$ (film thickness: 200 nm); and its substrate was made of silicon). The FET characteristic was measured with a semiconductor parameter analyzer (trade name: 4156C, manufactured by Agilent Co,) to which a semiautomatic prober (trade name: AX-2000, manufactured by Vector Semiconductor Co., Ltd.) was connected, under normal pressure in a nitrogen atmosphere (in a glove box). A result of the examination or observation of the FET characteristic demonstrated that the exemplified compound 1 exhibited a behavior characteristic for an ambipolar transistor. The characteristic is that the drain current becomes small in each of a p-type mode and in an n-type mode when the gate voltage is made large (FIGS. 6(a) and 6(b)).

Comparative Example

An element was prepared and the FET characteristic thereof was examined in the same way as described above except that the compound for comparison 1 was used instead of the exemplified compound 2. However, the element never exhibited any FET characteristic in a p-type mode nor n-type mode. From the result of the observation with the polarizing microscope, it appears that the film made of the compound for comparison 1 was an amorphous film and a FET characteristic was not exhibited at all since the orientation or alignment of the molecules was at random.

Example 3

(Characteristic of Organic Thin-Film Photoelectric Conversion Device)

A glass substrate (2.5 cm×2.5 cm) having thereon a patterned ITO electrode was washed with ultrasonic waves in isopropyl alcohol, and then dried. Furthermore, in order to remove any organic pollutants on the ITO electrode surface, the substrate was treated with UV ozone for 30 minutes. Next, the ITO substrate was spin-coated (at 4000 rpm for 60 seconds) with a solution of PEDOT (poly(3,4-ethylenedioxythiophene))/PSS (polystyrenesulfonic acid) in water (Baytron P (standard product)), and then the whole was dried at 120° C. for 10 minutes to form a hole-transporting buffer layer having a film thickness of about 50 nm. The film thickness was measured with a probe-used thickness meter (trade name: DEKTAK 6M, manufactured by ULVAC, Inc.) [the same matter will be correspondingly applied to the following description]. Next, a 1.0 mg/mL solution of the exemplified compound 2 in chloroform was drop-cast onto the buffer layer to form a photoelectric conversion layer having an even thickness of 500 nm or less. A vacuum evaporation machine (trade name: EBX-8C, manufactured by ULVAC, Inc.) was used to vacuum-evaporate aluminum toward the photoelectric conversion layer at a vacuum degree of $2\times10^{-4}$ or less to form metal electrodes having a thickness of about 80 nm on the photoelectric conversion layer. Lastly, in a nitrogen atmosphere inside a glove box, a sealing can made of glass and a UV curable resin were used to enclose the workpiece into the can, thereby yielding an organic thin-film photoelectric conversion device having an effective area of 0.04 cm². A photoelectric conversion layer formed under the same conditions was observed with a polarizing microscope. As a result, optical anisotropy was observed, and the average domain size was 1 μm or more.

Figure 7:
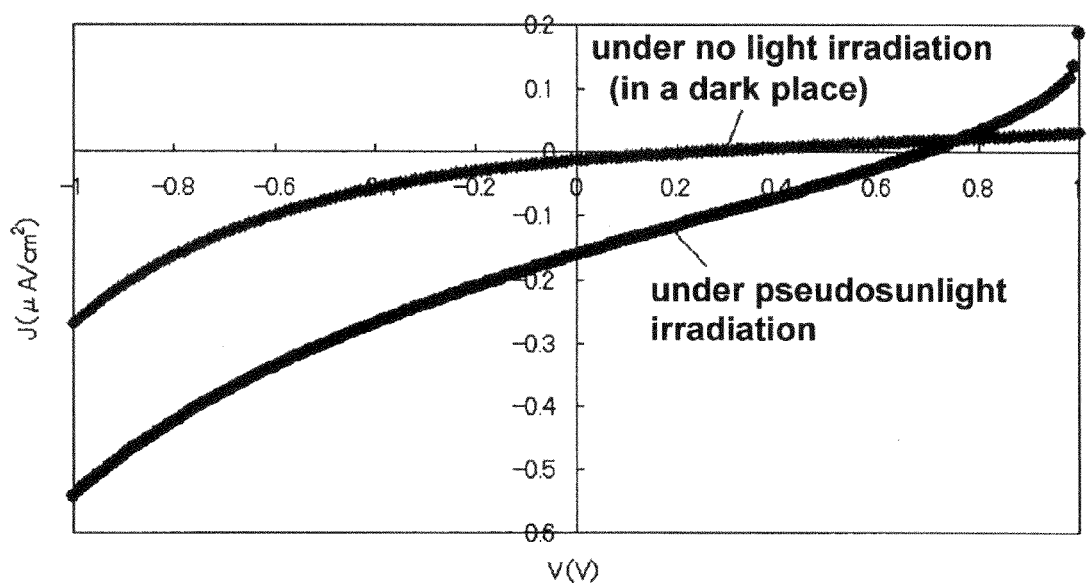
FIG. 7 is a chart showing the photoelectric conversion property of an organic thin-film photoelectric conversion device using the exemplified compound 2, which is a liquid crystalline organic semiconductor material of the present invention.

A solar simulator (150-W simple model, manufactured by Oriel Co.) was used to radiate pseudo-sunlight of 100 mW/cm² power (AM: 1.5) onto the element, and an electrochemical analyzer (trade name:. ALS MODEL 660B, manufactured by BAS Co.) was used to measure the current-voltage characteristic thereof. As a result, photoelectric current and photoelectromotive force were ascertained as illustrated in FIG. 7. The short-circuit current ($J_{sc}$) was 161 nA/cm², and the open voltage ($V_{OC}$) was 0.70 V.

Comparative Example

An organic thin-film photoelectric conversion device was prepared in the very same as in Example 1 except that the compound for comparison 1 was used instead of the exemplified compound 2. The conversion device did not respond at all to the pseudo-sunlight. A photoelectric conversion layer formed under the same conditions was observed with a polarizing microscope. As a result, it was made clear that the layer was an amorphous film. It appears that in the case of using a compound essential for the invention, the molecular orientation or alignment thereof is controlled by liquid crystallinity so that a hole transporting path and an electron transporting path are formed while in the case of using the compound for comparison 1 exhibiting no liquid crystallinity, the molecular orientation or alignment order is low so that no carrier path is formed.

Example 4

An organic thin-film photoelectric conversion device was produced in the same way as in Example 3 except that a 1.0 mg/mL solution of a mixture of the exemplified compound 2 and PCBM (ratio by weight: 1/1) in chloroform was used to form a photoelectric conversion layer instead of the 1.0 mg/mL solution of the exemplified compound 2 in chloroform, which was used to paint the exemplified compound 2 for the formation of the film, LiF was then vacuum-evaporated to form an electron-transporting buffer layer having a thickness of about 1 nm, and subsequently aluminum was vacuum-evaporated toward the buffer layer. In this conversion device also, photoelectric current and photoelectromotive force were generated by the irradiation with the pseudo-sunlight, so that a good photoelectric conversion property was exhibited.

As described above, it has been demonstrated that the organic semiconductor material of the invention exhibits the property of transporting two carrier species (holes and electrons) and photoelectric conversion property by the component alone, and thus the material is an excellent organic semiconductor material.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2008-160819 filed in Japan on Jun. 19, 2008, which is entirely herein incorporated by reference.

What I claim is:

1. A liquid crystalline organic semiconductor material, comprising a thermotropic liquid crystalline compound having at least one bonding form selected from the group consisting of (p-type organic semiconductor compound residue)-(n-type organic semiconductor compound residue)-(p-type organic semiconductor compound residue), and (n-type organic semiconductor compound residue)-(p-type organic semiconductor compound residue)-(n-type organic semiconductor compound residue), wherein the phase transition temperature of the liquid crystalline compound between a liquid crystal phase and an isotropic liquid phase in a temperature raising step is 200° C. or higher.

2. An organic semiconductor material for organic thin-film transistor, which comprises the liquid crystalline organic semiconductor material according to claim 1.

3. An organic semiconductor material for an organic thin-film photoelectric conversion device, which comprises the liquid crystalline organic semiconductor material according to claim 1.

4. A thin film comprising the liquid crystalline organic semiconductor material according to claim 1.

5. The thin film according to claim 4, wherein the film is formed by a wet film forming process.

6. The thin film according to claim 4, wherein an average domain size of a liquid crystal or crystal of the liquid crystalline organic semiconductor material is larger than a thickness of the film.

7. A liquid crystalline organic semiconductor material, comprising a thermotropic liquid crystalline compound having at least one bonding form selected from the group consisting of (p-type organic semiconductor compound residue)-(n-type organic semiconductor compound residue)-(p-type organic semiconductor compound residue), and (n-type organic semiconductor compound residue)-(p-type organic semiconductor compound residue)-(n-type organic semiconductor compound residue), wherein the n-type organic semiconductor compound residue in the liquid crystalline compound is any one of a naphthalenetetracarbonyl compound residue, perylenetetracarbonyl compound residue, and a terrylenetetracarbonyl compound residue.

8. A liquid crystalline organic semiconductor material, comprising a thermotropic liquid crystalline compound having at least one bonding form selected from the group consisting of (p-type organic semiconductor compound residue)-(n-type organic semiconductor compound residue)-(p-type organic semiconductor compound residue), and (n-type organic semiconductor compound residue)-(p-type organic semiconductor compound residue)-(n-type organic semiconductor compound residue), wherein the p-type organic semiconductor compound residue in the liquid crystalline compound is a triphenylamine residue.

9. A liquid crystalline organic semiconductor material, comprising a thermotropic liquid crystalline compound having at least one bonding form selected from the group consisting of (p-type organic semiconductor compound residue)-(n-type organic semiconductor compound residue)-(p-type organic semiconductor compound residue), and (n-type organic semiconductor compound residue)-(p-type organic semiconductor compound residue)-(n-type organic semiconductor compound residue), wherein the liquid crystalline compound is represented by any one of Formulae 1 to 3:

Formula 1

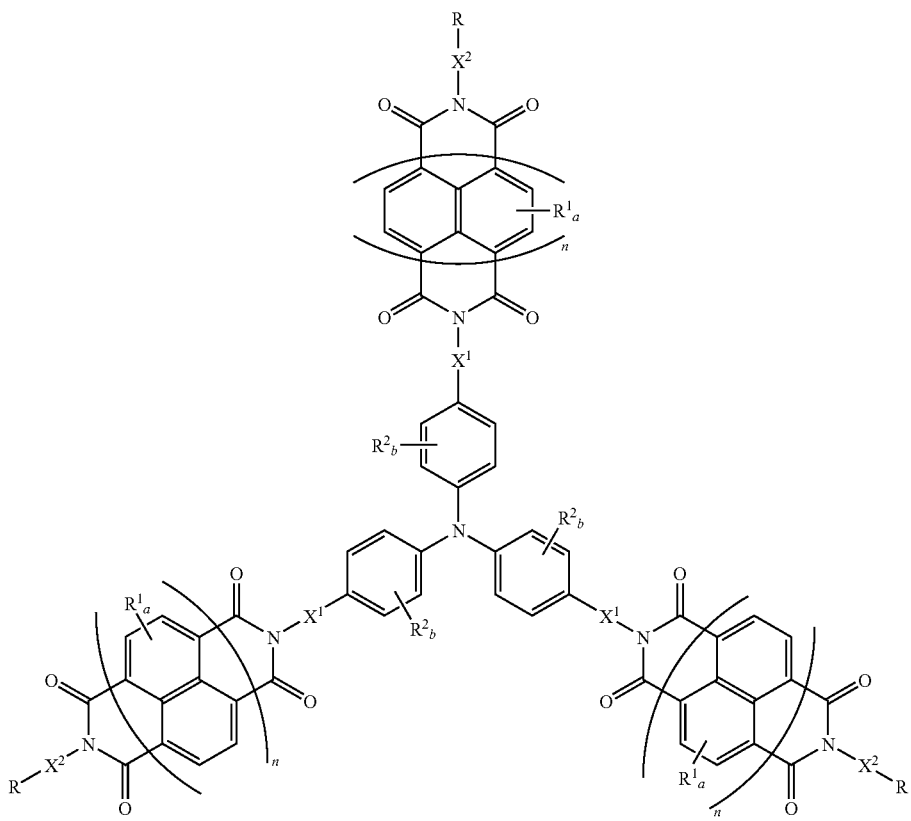

Formula 2

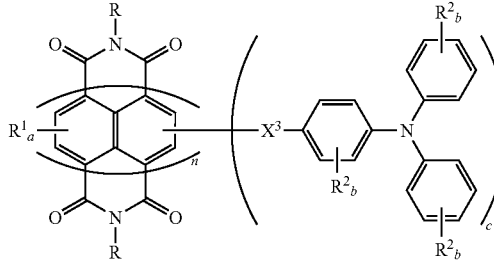

Formula 3

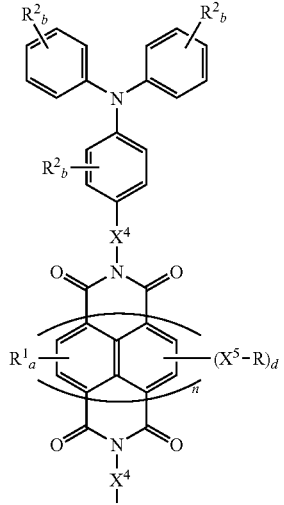

-continued

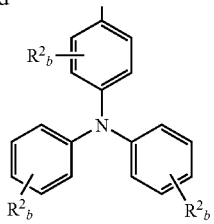

wherein R and $R^1$ each independently represents a hydrogen atom or a substituent; $X_1$, $X_2$, $X_3$, $X_4$, and $X_5$ each independently represents a single bond or a divalent linking group; a, b, c, and d each denotes an integer; n denotes an integer of 1 to 3;

$R^2$ represents a halogen atom, an alkyl group having 5 to 20 carbon atoms, an alkenyl group, an alkynyl group, an aryl group, a heterocyclic group, a cyano group, a hydroxyl group, a nitro group, a carboxyl group, an alkoxy group, an aryloxy group, a silylyoxy group, a heterocyclic oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkylsufonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsufonyl group, an arylsufonyl group, an acyl group, an aryloxycarbonyl group, an alkoxycarbonyl group, a carbomoyl group, an arylazo group, a heterocyclic azo group, an imido group, a phoshino group, a phosphyinyl group, a phosphinyloxy group, a phosphinylamino group, a phosphono group, a silyl group, a hydrazino group, an ureido group, a boronic acid group, a phosphate group, and a sulfate group, and in the case of a plurality of R, $R^1$, $R^2$, $X_1$, $X_2$, $X_3$, $X_4$, or $X_5$, they may be the same or different.

10. The liquid crystalline organic semiconductor material according to claim 9, wherein a length of the linking group represented by $X^1$, $X^3$ and $X^4$ each independently corresponds to 0 to 6 number of atom(s) provided that "number atom(s): 0" means a single bond.

11. A liquid crystal compound represented by any one of Formulae 1 to 3:

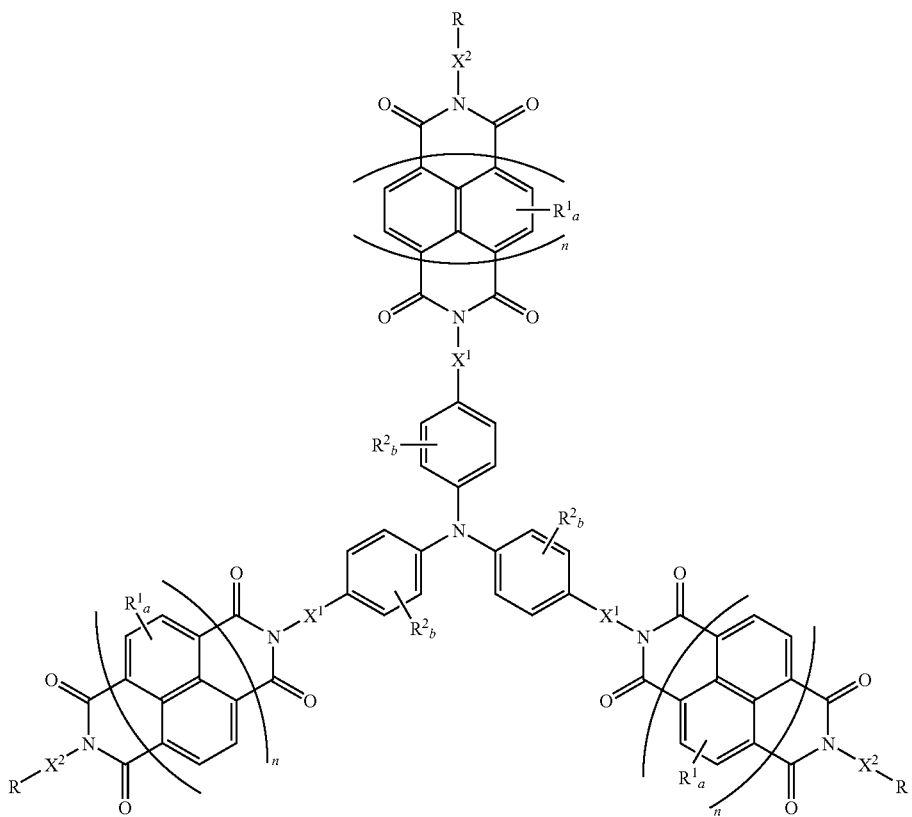

Formula 1

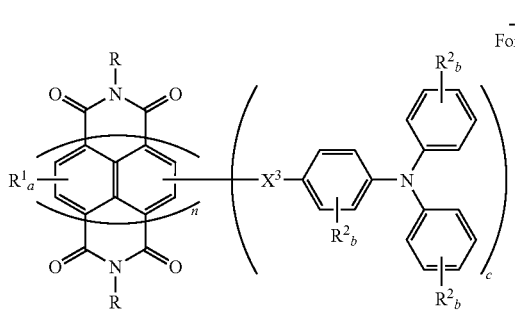

Formula 2

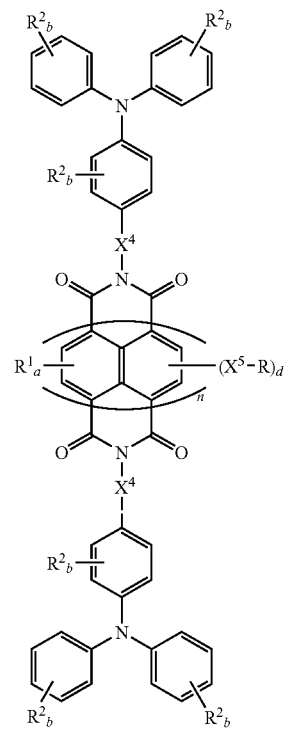

Formula 3 wherein R and $R^1$ each independently represents a hydrogen atom or a substituent; $X_1$, $X_2$, $X_3$, $X_4$, and $X_5$ each independently represents a single bond or a divalent linking group; a, b, c, and d each denotes an integer; n denotes an integer of 1 to 3;

$R^2$ represents a halogen atom, an alkyl group having 5 to 20 carbon atoms, an alkenyl group, an alkynyl group, an aryl group, a heterocyclic group, a cyano group, a hydroxyl group, a nitro group, a carboxyl group, an alkoxy group, an aryloxy group, a silylyoxy group, a heterocyclic oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkylsufonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsufonyl group, an arylsufonyl group, an acyl group, an aryloxycarbonyl group, an alkoxycarbonyl group, a carbomoyl group, an arylazo group, a heterocyclic azo group, an imido group, a phoshino group, a phosphyinyl group, a phosphinyloxy group, a phosphinylamino group, a phosphono group, a silyl group, a hydrazino group, an ureido group, a boronic acid group, a phosphate group, and a sulfate group, and in the case of a plurality of R, $R^1$, $R^2$, $X_1$, $X_2$, $X_3$, $X_4$, or $X_5$, they may be the same or different.

12. An organic electronic device, utilizing a thermotropic liquid crystalline organic semiconductor material that comprises, in the molecule thereof, a p-type organic semiconductor compound residue and a n-type organic semiconductor compound residue, wherein the phase transition temperature of the liquid crystalline organic semiconductor material between a liquid crystal phase and an isotropic liquid phase in a temperature raising step is 200° C. or higher.

13. The organic electronic device according to claim 12, wherein an average domain size of a liquid crystal or crystal of the liquid crystalline organic semiconductor material is larger than a distance between electrodes of the device.

14. The organic electronic device according to claim 12, wherein the organic electronic device is an organic thin-film transistor.

15. The organic electronic device according to claim 12, wherein the organic electronic device is an organic thin-film photoelectric conversion device.

16. The organic electronic device according to claim 12, wherein the organic electronic device comprises an electron-transporting buffer layer between at least one semiconductor active layer and at least one electrode.

17. The organic electronic device according to claim 12, wherein the organic electronic device comprises a hole-transporting buffer layer between at least one semiconductor active layer and at least one electrode.

18. The organic electronic device according to claim 12, wherein a film thickness of a semiconductor active layer is 1 nm or more and 1 μm or less.

19. The organic electronic device according to claim 12, wherein a semiconductor active layer is formed by a wet film forming process.

20. The organic electronic device according to claim 12, wherein the liquid crystalline organic semiconductor material is sealed in an inert gas atmosphere.

21. An organic electronic device, utilizing a liquid crystalline organic semiconductor material that comprises a thermotropic liquid crystalline compound having at least one bonding form of (p-type organic semiconductor compound residue)-(n-type organic semiconductor compound residue), wherein the phase transition temperature of the liquid crystalline compound between a liquid crystal phase and an isotropic liquid phase in a temperature raising step is 200° C. or higher.

22. The organic electronic device according to claim 21, wherein the liquid crystalline organic semiconductor material comprises a thermotropic liquid crystalline compound having at least one bonding form selected from the group consisting of (p-type organic semiconductor compound residue)-(n-type organic semiconductor compound residue)-(p-type organic semiconductor compound residue), and (n-type organic semiconductor compound residue)-(p-type organic semiconductor compound residue)-(n-type organic semiconductor compound residue).

23. The organic electronic device according to claim 21, wherein an average domain size of a liquid crystal or crystal of the liquid crystalline organic semiconductor material is larger than a distance between electrodes of the device.

24. The organic electronic device according to claim 21, wherein the organic electronic device is an organic thin-film transistor.

25. The organic electronic device according to claim 21, wherein the organic electronic device is an organic thin-film photoelectric conversion device.

26. The organic electronic device according to claim 21, wherein the organic electronic device comprises an electron-transporting buffer layer between at least one semiconductor active layer and at least one electrode.

27. The organic electronic device according to claim 21, wherein the organic electronic device comprises a hole-transporting buffer layer between at least one semiconductor active layer and at least one electrode.

28. The organic electronic device according to claim 21, wherein a film thickness of a semiconductor active layer is 1 nm or more and 1 μm or less.

29. The organic electronic device according to claim 21, wherein a semiconductor active layer is formed by a wet film forming process.

30. The organic electronic device according to claim 21, wherein the liquid crystalline organic semiconductor material is sealed in an inert gas atmosphere.

* * * * *